US012016339B2

(12) United States Patent
Naudet et al.

(10) Patent No.: US 12,016,339 B2
(45) Date of Patent: Jun. 25, 2024

(54) CONTROL OF PLANT PESTS USING RNA MOLECULES

(71) Applicant: SYNGENTA PARTICIPATIONS AG, Basel (CH)

(72) Inventors: Yann Naudet, Ghent (BE); Myriam Beghyn, Ghent (BE); Lien De Schrijver, Ghent (BE); Annelies Philips, Ghent (BE); Isabelle Maillet, Ghent (BE)

(73) Assignee: SYNGENTA PARTICIPATIONS AG, Basel (CH)

( * ) Notice: Subject to any disclaimer, the term of this patent is extended or adjusted under 35 U.S.C. 154(b) by 125 days.

(21) Appl. No.: 16/756,232

(22) PCT Filed: Nov. 6, 2018

(86) PCT No.: PCT/US2018/059383
§ 371 (c)(1),
(2) Date: Apr. 15, 2020

(87) PCT Pub. No.: WO2019/094368
PCT Pub. Date: May 16, 2019

(65) Prior Publication Data

US 2021/0186029 A1 Jun. 24, 2021

(30) Foreign Application Priority Data

Nov. 13, 2017 (GB) .................................... 1718701

(51) Int. Cl.
*C12N 15/113* (2010.01)
*A01N 63/60* (2020.01)

(52) U.S. Cl.
CPC ........... *A01N 63/60* (2020.01); *C12N 15/113* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 9,238,822 | B2 | 1/2016 | Baum et al. | |
| 2006/0058254 | A1* | 3/2006 | Dina | C07H 21/00 514/44 R |
| 2006/0287267 | A1* | 12/2006 | Vaish | C12N 15/1131 544/243 |
| 2007/0031844 | A1* | 2/2007 | Khvorova | A61P 35/00 435/6.11 |
| 2012/0240288 | A1 | 9/2012 | Jian et al. | |
| 2013/0291188 | A1 | 10/2013 | Bogart et al. | |
| 2015/0004148 | A1 | 1/2015 | Raemaekers et al. | |
| 2015/0240258 | A1 | 8/2015 | Beattie et al. | |
| 2016/0060628 | A1 | 3/2016 | Beghyn et al. | |
| 2017/0260522 | A1* | 9/2017 | Crawford | C12N 15/113 |
| 2017/0283828 | A1 | 10/2017 | Baum et al. | |

FOREIGN PATENT DOCUMENTS

| | | | |
|---|---|---|---|
| CN | 103849625 | A | 6/2014 |
| RU | 2015101749 | A | 8/2016 |
| WO | 2007035650 | A2 | 3/2007 |
| WO | 2012055982 | A2 | 5/2012 |
| WO | 2015010026 | A2 | 1/2015 |
| WO | 2016018887 | A1 | 2/2016 |
| WO | 2016060911 | A1 | 4/2016 |
| WO | 2016060912 | A2 | 4/2016 |
| WO | 2016060913 | A1 | 4/2016 |
| WO | 2016118762 | A1 | 7/2016 |
| WO | 2017106171 | A1 | 6/2017 |
| WO | 2017132330 | A1 | 8/2017 |

OTHER PUBLICATIONS

International Search Report for International Application No. PCT/US2018/059383 dated Mar. 8, 2019.

Zhu, Fang et al., "Ingested RNA Interference for Managing the Populations of the Colorado Potato Beetle, Leptinotarsa Decemlineata", Pest Management Science, vol. 67, No. 2, Nov. 8, 2010, pp. 175-182.

Baum, James A. et al., "Control of Coleopteran Insect Pests Through RNA Interference", Nature Biotechnology, vol. 25, No. 11, Nov. 4, 2007, pp. 1322-1326.

Vogel, H. et al., "RNA-Sequencing Analysis Reveals Abundant Developmental Stage-Specific and Immunity-Related Genes in the Pollen Beetle Meligethes Aeneus", Insect Molecular Biology, vol. 23, No. 1, Nov. 20, 2013, pp. 98-112.

Vallier, Agnés et al., "RNAi in the Cereal Weevil Sitophilus SPP: Systemic Gene Knockdown in the Bacteriome Tissue", BMC Biotechnology, vol. 9, No. 1, May 15, 2009, p. 44.

Mamta, B. et al., "RNAi Technology: A New Platform for Crop Pest Control", Physiology and Molecular Biology of Plants, vol. 23, No. 3, Apr. 29, 2017, pp. 487-501.

Edde, Peter A., "A Review of the Biology and Control of *Rhyzopertha dominca* (F.) the Lesser Grain Borer", Journal of Stored Products Research, vol. 48, Nov. 28, 2011, pp. 1-18.

Zhao, Y.Y. et al., "PsOr1, a Potential Target for RNA Interference-based Pest Management", Insect Molecular Biology, vol. 20, No. 1, Sep. 21, 2010, pp. 97-104.

Klys, Malgorzata et al., "The Repellent Effect of Plants and Their Active Substances Against the Beetle Storage Pests", Journal of Stored Products Research, vol. 74, Oct. 16, 2017, pp. 66-77.

Zhang, Han et al., "Arthropod Pest Control for UK Oilseed Rape—Comparing Insecticide Efficacies, Side Effects and Alternatives", PLOS ONE, vol. 12, No. 1, Jan. 11, 2017, p. e0169475.

(Continued)

*Primary Examiner* — Brian Whiteman
(74) *Attorney, Agent, or Firm* — BakerHostetler; Toni-Junell Herbert

(57) ABSTRACT

Disclosed are double stranded RNA (dsRNA) molecules that are toxic to insect pests. In particular, interfering RNA molecules capable of modulating expression of a pest insect target gene and that are toxic to the insect pest are provided. Further, methods of making and using the interfering RNA, for example as the active ingredient in an insecticidal composition or in a transgenic plant, to confer protection from insect damage are disclosed.

15 Claims, No Drawings

Specification includes a Sequence Listing.

(56) References Cited

OTHER PUBLICATIONS

Willow, Jonathan et al., "Targeting a Coatomer Protein Complex-I Gene via RNA Interference Results in Effective ethality in the Pollen Beetle *Brassicogethes aeneus*", Journal of Pest Science, vol. 94, No. 3, Nov. 16, 2020, pp. 703-712.
Extended European Search Report in Application No. EP 18876328.8, dated Feb. 9, 2022.
Fang Zhu et al., Ingested RNA Interference for Managing the Populations of the Colorado Potato Beetle, Pest Management Science, vol. 67, No. 2, (2011), pp. 175-182.
James Baum, et al., Control of Coleopteran Insect Pests through RNA Interference, Nature Biotechnology, vol. 25, No. 11, (2007), pp. 1322-1326.
Supplementary Partial European Search Report for EP Application No. 18876328.8 dated Sep. 7, 2021.
Chan W. et al.: "The complexity of antisense transcription revealed by the study of developing male germ cells", Genomics, 2006, vol. 87, Issue 6, pp. 681-692.
Ibargutxi M. A. et al.: "Use of Bacillus thuringiensis Toxins for Control of the Cotton Pest *Earias insulana* (Boisd.) (Lepidoptera: Noctuidae)", Applied and Environmental Microbiology, 2006, vol. 72, No. 1, pp. 437-442.
Lapidot M. et al.: "Genome-wide natural antisense transcription: coupling its regulation to its different regulatory mechanisms", EMBO Rep., 2006, vol. 7, N.12, pp. 1216-1222.
Office Action for Russian Patent Application No. 2020 118 310 dated Mar. 1, 2022.
Office Action for Russian Patent Application No. 2020 118 310 dated Jul. 21, 2022.
Rodrigues et al., Development of RNAI method for screening candidate genes to control emerald ash borer, *Agrilus planipennis*, Scientific Reports | 7: 7379.
Rospatent; RU Counterpart App. No. 2020 118 310; Russian Office Action dated Dec. 16, 2022; pp. 1-16.
Bolognesi et al.; (2012); "Characterizing the Mechanism of Action of Double-Stranded RNA Activity against Western Corn Rootworm (*Diabrotica virgifera virgifera* LeConte)."; PLoS ONE 7(10): e47534. https://doi.org/10.1371/journal.pone.0047534.
Russian Office Action issued in Russian Patent Application No. 2020 118 310 dated May 5, 2023, with English translation.
Chellappan, et al., "siRNAs from miRNA sites mediate DNA methylation of target genes", Nucleic Acids Research, vol. 38, No. 20, pp. 6883-6894, 2010.
Preliminary conclusion of the qualification examination issued in Ukrainian Patent Application No. 2020 03356 dated Nov. 20, 2023, with English translation.

* cited by examiner

CONTROL OF PLANT PESTS USING RNA MOLECULES

RELATED APPLICATION INFORMATION

This application is a 371 of International Application No. PCT/US2018/059383, filed Nov. 6, 2018, which claims priority to GB 1718701.4, filed Nov. 13, 2017, the contents of each of which are incorporated herein by reference herein.

SEQUENCE LISTING

A Sequence Listing in ASCII text format, submitted under 37 C.F.R. § 1.821, entitled "P304007US amended sequence listing 14474853.txt" 84 kilobytes in size, generated on Dec. 11, 2023, and filed via EFS-Web is provided in lieu of a paper copy. This Sequence Listing is hereby incorporated by reference into the specification for its disclosures in its entirety.

FIELD OF THE INVENTION

The invention relates generally to the control of pests that cause damage to crop plants by their feeding activities, and more particularly to the control of at least coleopteran insect pests by compositions comprising interfering RNA molecules. The invention further relates to the compositions and to methods of using such compositions comprising the interfering RNA molecules.

BACKGROUND

Commercial crops are often attacked by invertebrate pests such as insects. Compositions for controlling insect infestations in plants have typically been in the form of chemical insecticides. Good insect control can thus be reached, but these chemicals can sometimes also affect other, beneficial insects. Additional problems occur in areas of high insecticide use where populations of pest insects have become resistant to certain insecticides. This has been partially alleviated by various resistance management practices, but there is an increasing need for alternative pest control agents.

Insecticidal compositions that include the bacteria *Bacillus thuringiensis* ("Bt") have been commercially available and used as environmentally safe and acceptable bio-insecticides for more than thirty years. The effectiveness of these compositions is due to insecticidal proteins (called "Cry proteins") that are produced during the sporulation phase of the bacteria's growth cycle. Cry proteins are primarily active against the larval stages of pest insects and not active against the adult stage. Several native Cry proteins from Bt, for example, Cry1Ab, Cry1F, Cry2Aa and Cry34/Cry35, or engineered Cry proteins, for example modified Cry3A (mCry3A) or eCry3.1Ab, have also been expressed in transgenic crop plants, for example corn, and exploited commercially to control certain lepidopteran and coleopteran insect pests.

With the increased use of transgenic plants expressing Cry proteins, there have now been some reports that populations of pest insects in certain geographies have become tolerant or resistant to certain Cry proteins. Therefore, identifying alternative insect control agents with new modes of action, i.e. different from existing chemical insecticides and Cry proteins, would be beneficial. In addition, new biological insect control agents that may be toxic to multiple life stages of the target insect pest would be useful. Such insect control agents may include those that target genetic elements, such as genes that are essential to the growth and/or survival of a target insect pest.

RNA interference (RNAi) is a well-established technique to regulate gene expression, for example to down regulate gene expression, by using double-stranded RNA (dsRNA) or small interfering RNA (siRNA) to trigger degradation of messenger RNA (mRNA) of a gene of interest, thus preventing translation of a protein. RNAi has not only provided a means of functionally analyzing genes, but has been used for the effective control of pests, in particular plant insect pests. RNAi occurs when an organism recognizes ds RNA molecules and hydrolyzes them. The resulting hydrolysis products are siRNA fragments of about 19-24 nucleotides in length. The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of, their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

RNAi has been found to be useful for control of certain insect pests. RNAi strategies typically employ a synthesized, non-naturally occurring "interfering RNA", or "interfering RNA molecule" which typically comprises at least a RNA fragment against a target gene, a spacer sequence, and a second RNA fragment which is complementary to the first, so that a dsRNA structure can be formed. This non-naturally occurring dsRNA takes advantage of the native RNAi pathways in the insect to trigger down-regulation of target genes that may lead to the cessation of feeding and/or growth and may result in the death of the insect pest.

Although it is known in the literature that RNAi strategies focused on certain target genes can lead to an insecticidal effect, for example in *Diabrotica* (corn rootworm) species, it is also known that not every target sequence is successful, and that an insecticidal effect cannot be predicted. For example, the overwhelming majority of sequences complementary to corn rootworm DNAs are not lethal in species of corn rootworm when used as dsRNA or siRNA. For example, Baum et al. ((2007) Nature Biotechnology 25:1322-1326), describe the effects of inhibiting several western corn rootworm (WCR) gene targets by RNAi. These authors reported that 8 of 26 target genes they tested were not able to provide experimentally significant WCR mortality, even at a very high concentration of more than 520 ng/cm$^2$ of interfering RNA (e.g. dsRNA). Additionally, target genes against which a dsRNA molecule is known to give a strong RNAi effect in one insect species may not be a good target for different insect species. Whyard et al. ((2009) *Insect Biochemistry and Molecular Biology* 39: 824-832) report nearly 100-fold differences in efficacy when testing conspecific dsRNA molecules against a V-ATPase gene in four different insect species.

There is an ongoing need for compositions containing insecticidal active ingredients, and for methods of using such compositions, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against the larval and/or adult stages of the pest insect. Thus any invention which provided compositions in which any of these properties was enhanced would represent a step forward in the art.

SUMMARY

The needs outlined above are met by the present invention which, in various embodiments, provides new compositions and methods of controlling economically important insect pests. More particularly, the invention provides compositions and methods of inhibiting expression of one or more target genes and proteins in at least coleopteran pests. More particularly, the invention provides compositions and methods of modulating expression of a beta-coatomer target gene, designated herein as beta-COP, in coleopteran insect pests, such as *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata* and related species, that causes cessation of feeding, growth, development and reproduction, and eventually results in the death of the insect. A method of the invention comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more target genes and wherein inhibition of the one or more target genes exerts a deleterious effect upon the pest insect. The interfering RNA molecule is non-naturally occurring. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that, when delivered to a pest insect, inhibits through a toxic effect the ability of the pest insect to survive, grow, feed and/or reproduce, or to limit pest related feeding damage or loss to crop plants. Such delivery may be by topically applying a composition comprising the interfering RNA to a plant, or to a plant part, such as a plant seed or a plant root. Such delivery may also be through production of the interfering RNA in a transgenic plant. The interfering RNA may also be provided in an artificial insect diet which the insect then contacts by feeding. The interfering RNA molecule comprises a nucleotide sequence that is complementary to a nucleotide sequence of a mRNA transcribable from a target gene or a portion of a nucleotide sequence of a mRNA transcribable from a target gene of the pest insect and therefore inhibits expression of the target gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

Accordingly, nucleic acid molecules comprising the sequence of beta-COP from multiple insect pest species are disclosed herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. In addition, nucleic acid molecules comprising the complement of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9 are disclosed. Specific fragments of these sequences are also disclosed herein as SEQ ID NO: 11, SEQ ID NO:12, SEQ ID NO:13, SEQ ID NO:14, SEQ ID NO:15, SEQ ID NO:16, SEQ ID NO:17, SEQ ID NO:18 or SEQ ID NO:19. The sequences of beta-COP and/or a fragment thereof can be targeted by an interfering RNA of the invention which may cause cessation of feeding, growth, development and/or reproduction of a pest insect, and eventually results in the death of the pest insect.

In one aspect of the invention, an interfering RNA molecule is provided wherein the interfering RNA is encoded by a sequence comprising, consisting essentially of or consisting of (a) any one of SEQ ID NOs:1-9; (b) the complement of any one of SEQ ID NOs:1-9; (c) at least 19 consecutive nucleotides of any one of SEQ ID NOs:1-9; (d) the complement of at least 19 consecutive nucleotides of any one of SEQ ID NOs:1-9; or (e) a sequence that hybridizes under stringent conditions with any of the aforementioned sequences, wherein the interfering RNA molecule post-transcriptionally silences an essential gene in at least a coleopteran pest insect and wherein the RNA encoding sequence is not a sequence comprising SEQ ID NO:10, the complement of SEQ ID NO:10, any at least 19 nucleotide fragment of SEQ ID NO:10, the complement of any at least 19 nucleotide fragment of SEQ ID NO:10 or a sequence that hybridizes under stringent conditions with SEQ ID NO:10, or the complement or a fragment thereof.

In another aspect, the invention provides a double-stranded RNA (dsRNA) comprising annealed complementary strands, one strand of which comprises a sequence of at least 19 consecutive nucleotides which is wholly or partially complementary to a portion of a mRNA polynucleotide transcribable from a pest insect target gene, wherein the pest insect target gene comprises a coding sequence having from at least 90% to at least 99% identity to any of SEQ ID NOs:1-9, or comprises any of SEQID NOs:1-9, and wherein the strand of RNA having complementarity to the target gene is toxic to an insect pest, preferably to at least a coleopteran insect pest.

In another aspect of the invention, the inferring RNA or dsRNA is complementary to a portion of a target gene comprising, consisting essentially of or consisting of any of SEQ ID NOs:11-19.

In still another aspect of the invention, the inferring RNA or dsRNA comprises a nucleotide fragment that has at least 85% identity to any of SEQ ID NOs:38-46. In some embodiments of this aspect the inferring RNA or dsRNA comprises, consists essentially of or consists of any of SEQ ID NOs: 38-46.

In another aspect of the invention, the interfering RNA molecule has insecticidal activity on at least a coleopteran insect pest. In some embodiments of this aspect, the interfering RNA molecule may comprise, consist essentially of or consist of at least two dsRNAs, wherein each dsRNA comprises, consists essentially of or consists of a sequence of nucleotides which is at least partially complementary to a target nucleotide sequence within the target gene. In further embodiments, each of the dsRNAs may comprise a different sequence of nucleotides which is complementary to a different target nucleotide sequence within the target gene.

The invention further provides compositions comprising one or more interfering RNA molecules comprising, consisting essentially of or consisting of two or more dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of at least a coleopteran pest insect gene that comprises a dsRNA of the invention and an agriculturally acceptable carrier. In some embodiments of this aspect, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata*. In some embodiments, inhibition of the expression of a beta-COP target gene in a target insect pest of the invention leads to cessation of feeding and growth and ultimately results in the death of the target insect pest of the invention.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests can be controlled by a plant that produces an interfering RNA molecule of the invention or by a plant or plant seed that is treated with a composition comprising an interfering RNA molecule of the invention.

The invention also provides a method of controlling at least a coleopteran insect pest comprising contacting the insect pest with a nucleic acid molecule that is or is capable of producing an interfering RNA of the invention for inhibiting expression of a target gene in the insect pest thereby controlling the insect pest. In some aspects, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata*. In other aspects, the target gene is beta-COP.

In other aspects, the invention provides a method of reducing an insect pest population on a transgenic plant expressing a second insecticidal agent, for example an insecticidal protein, by applying to the transgenic plant a composition comprising an interfering RNA of the invention capable of inhibiting expression of an target gene in an insect pest, thereby reducing the pest insect population. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the second insecticidal agent may be derived from sources other than *B. thuringiensis*. The second insecticidal agent can be an agent selected from the group comprising a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporus* insecticidal protein, a *Lysinibacillus sphaericus* insecticidal protein, a *Chromobacterium* spp. insecticidal protein, a *Yersinia* entomophaga insecticidal protein, a *Paenibacillus popilliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabdus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporus* or BinA and BinB from *L. sphaericus*. In still other embodiments, the insecticidal protein may be engineered or may be a hybrid or chimera of any of the preceding insecticidal proteins.

In other aspects, the invention provides a method of reducing the level of a target RNA transcribable from a pest insect beta-COP target gene described herein comprising contacting the pest insect with a composition comprising an interfering RNA molecule of the invention, wherein the interfering RNA molecule reduces the level of the target RNA in a cell of the pest insect.

In still other aspects, the invention provides a method of conferring pest insect, particularly at least a coleopteran pest insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the pest insect.

In other aspects, the invention provides a method of enhancing control of at least a coleopteran insect population comprising applying to a plant or seed, or to a transgenic plant or a transgenic seed, a composition comprising an interfering RNA of the invention and a chemical pesticide that is insecticidal to at least a coleopteran insect, thereby enhancing control of the coleopteran insect population.

In another aspect, the invention provides a method of identifying a beta-COP gene in an insect pest for interfering RNA targeting, said method comprising the steps of: a) isolating nucleic acid from an insect pest; b) amplifying an orthologous beta-COP target gene from the nucleic acid with a pair of primers comprising nucleotide sequences selected from SEQ ID NOs:38-55; c) identifying a sequence of an orthologous beta-COP target gene; d) producing a dsRNA molecule, wherein the dsRNA molecule comprises a sense strand and an antisense strand, wherein a nucleotide sequence of the antisense strand is complementary to a portion of a mRNA polynucleotide transcribable from the insect pest beta-COP gene that comprises a beta-COP coding sequence, and e) testing the dsRNA molecule of step d) for insecticidal activity against the insect pest.

These and other aspects of the invention are set forth in more detail in the description of the invention below.

BRIEF DESCRIPTION OF THE SEQUENCES IN THE SEQUENCE LISTING

SEQ ID NOs:1-10 are pest insect beta-COP coding sequences.

SEQ ID NOs:11-19 are fragments of DNA coding sequences used to synthesize interfering RNA molecules to test for insecticidal activity.

SEQ ID NOs:20-28 are RNA sequences of the fragments of the DNA coding sequences used to synthesize interfering RNA molecules to test for insecticidal activity SEQ ID NOs:29-37 are RNA sequences of the complete DNA sequences of SEQ ID NOs:1-9.

SEQ ID NOs:38-55 are nucleotide sequences of forward and reverse primers used to identify target genes (SEQ ID NOs:1-9) from pest insects of the invention.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Definitions

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

For clarity, certain terms used in the specification are defined and presented as follows:

As used herein, "a," "an" or "the" can mean one or more than one. For example, "a cell" can mean a single cell or a multiplicity of cells.

As used herein, "and/or" refers to and encompasses any and all possible combinations of one or more of the associated listed items, as well as the lack of combinations when interpreted in the alternative, "or."

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

The terms "complementary" or "complementarity," refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. Complementary polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

To "deliver" a composition or toxic RNA means that the composition or toxic RNA comes in contact with an insect, which facilitates the oral ingestion of the composition or toxic RNA, resulting in a toxic effect and control of the insect. The composition or toxic RNA can be delivered in many recognized ways, including but not limited to, transgenic plant expression, formulated interfering RNA composition(s), sprayable interfering RNA composition(s), a bait matrix, or any other art-recognized RNA delivery system.

"Expression cassette" as used herein means a nucleic acid molecule capable of directing expression of at least one polynucleotide of interest, such as a polynucleotide that encodes an interfering RNA of the invention, in an appropriate host cell, comprising a promoter operably linked to the polynucleotide of interest which is operably linked to a termination signal. An "expression cassette" may also comprise additional polynucleotides required for proper translation of a polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Insecticidal" is defined as a toxic biological activity capable of controlling insects, preferably by killing them.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant. Therefore, a claim to an "isolated" nucleic acid molecule, as enumerated herein, encompasses a nucleic acid molecule when the nucleic acid molecule is comprised within a transgenic bacteria or plant genome.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on “identity” and “substantial identity”). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

The terms “sequence similarity” or “sequence identity” of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 consecutive nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The phrase “substantially identical,” in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff& Henikoff, *Proc. Nat. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Moderate stringency conditions detect sequences that share at least 80% sequence identity. Exemplary moderate stringency conditions include hybridization in 40 to 45% formamide, 1 M NaCl, 1% SDS at 37° C., and a wash in 0.5× to 1×SSC at 55 to 60° C. High stringency conditions detect sequences that share at least 90% sequence identity. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)−0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part 1, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

As used herein, "dsRNA" or "interfering RNA" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesized and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the percent identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. It is well-known in the art that small dsRNA of about 19-23 bp in length can be used to trigger gene silencing of a target gene. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 19 to about 23 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule. Bolognesi et al (2012, PLOS One, 7(10): e47534, herein incorporated by reference) teach that dsRNAs greater than or equal to about 60 bp are required for biological activity in artificial diet bioassays with Southern Corn Rootworm (SCR; *Diabrotica undecimpunctata howardii*).

Mao et al (2007, *Nature Biotechnology,* 35(11): 1307-1313) teach a transgenic plant expressing a dsRNA construct against a target gene (CYP6AE14) of an insect pest (cotton bollworm, *Helicoverpa armigera*). Insects feeding on the transgenic plant have small RNAs of about 19-23 bp in size of the target gene in their midgut, with a corresponding reduction in CYP6AE14 transcripts and protein. This suggests that the small RNAs were efficacious in reducing expression of the target gene in the insect pest. Therefore, small RNAs of about 19 bp, about 20 bp, about 21 bp, about 22 bp, about 23 bp, about 24 bp, about 25 bp, about 26 bp, about 27 bp, about 28 bp, about 29 bp, or about 30 bp may be efficacious in reducing expression of the target gene in an insect pest.

Alternatively, the dsRNA may comprise a target dsRNA of at least 19 base pairs, and the target dsRNA may be within a dsRNA "carrier" or "filler" sequence. For example, Bolognesi et al (2012) show that a 240 bp dsRNA encompassing a target dsRNA, which comprised a 21 bp consecutive sequence with 100% identity to the target sequence, had biological activity in bioassays with Southern Corn Rootworm. The present application exemplifies a similar approach in bioassays with Western Corn Rootworm. The target dsRNA may have a length of at least 19 to about 25 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs. Combined with the carrier dsRNA sequence, the dsRNA of the target sequence and the carrier dsRNA may have a total length of at least about 50 to about 100 base pairs, optionally a sequence of about 100 to about 200 base pairs, optionally a sequence of about 200 to about 500, and optionally a sequence of about 500 to about 1000 or more base pairs.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

The interfering RNAs of the invention may comprise one dsRNA or multiple dsRNAs, wherein each dsRNA comprises or consists of a sequence of nucleotides which is at least partially complementary to a target nucleotide sequence within the target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyzes processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell,* 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase, available via the World Wide Web). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim *Nature Rev. Mol. Cell Biol.* 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*, e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a formulated product comprising the dsRNA of the invention that is topically applied to a plant or plant part such as a seed, or such composition may be a transgenic plant expressing the dsRNA of the invention.

The term "agrochemically active ingredient" refers to chemicals and/or biological compositions, such as those described herein, which are effective in killing, preventing, or controlling the growth of undesirable pests, such as, plants, insects, mice, microorganism, algae, fungi, bacteria, and the like (such as pesticidal active ingredients). An interfering RNA molecule of the invention is an agrochemically active ingredient.

An "agriculturally acceptable carrier" includes adjuvants, mixers, enhancers, etc. beneficial for application of an active ingredient, such as an interfering RNA molecule of the invention. Suitable carriers should not be phytotoxic to valuable crops, particularly at the concentrations employed in applying the compositions in the presence of crops, and should not react chemically with the compounds of the active ingredient herein, namely an interfering RNA of the invention, or other composition ingredients. Such mixtures can be designed for application directly to crops, or can be concentrates or formulations which are normally diluted with additional carriers and adjuvants before application. They may include inert or active components and can be solids, such as, for example, dusts, granules, water dispersible granules, or wettable powders, or liquids, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

For the invention, an agriculturally acceptable carrier may also include non-pathogenic, attenuated strains of microorganisms, which carry the insect control agent, namely an interfering RNA molecule of the invention. In this case, the microorganisms carrying the interfering RNA may also be referred to as insect control agents. The microorganisms may be engineered to express a nucleotide sequence of a target gene to produce interfering RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the interfering RNA molecules or fragments or derivatives thereof.

In another embodiment, the interfering RNA molecules may be encapsulated in a synthetic matrix such as a polymer and applied to the surface of a host such as a plant. Ingestion of the host cells by an insect permits delivery of the insect control agents to the insect and results in down-regulation of a target gene in the host.

A composition of the invention, for example a composition comprising an interfering RNA molecule of the invention and an agriculturally acceptable carrier, may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing: and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUGCAUGCU (SEQ ID NO: 56) is a "19 mer."

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated herein by their bases by the following standard abbreviations: adenine (A), cytosine (C), thymine (T), guanine (G) and uracil (U).

The invention is based on the unexpected result that double stranded RNA (dsRNA) or small interfering RNAs (siRNA) designed to target a mRNA transcribable from a pest insect essential gene, particularly a beta coatomer ("beta-COP") essential gene described herein, are toxic to the pest insect and can be used to control pest insect infestation of a plant and impart to a transgenic plant tolerance to a pest insect infestation, particularly a coleopteran pest insect infestation. An interfering RNA molecule of the invention does not occur in nature. Thus, in some aspects, the invention provides a dsRNA molecule comprising a sense strand and an antisense strand, wherein a nucleotide sequence of the antisense strand is complementary to a portion of a mRNA polynucleotide transcribable from a pest insect beta-COP gene described herein, wherein the dsRNA molecule is toxic to a pest insect, particularly to at least a coleopteran pest insect.

Nucleic acid molecules comprising the sequence of beta-COP from multiple insect pest species are disclosed herein as SEQ ID NOs:1-9. Specific fragments of these sequences are also disclosed herein as SEQ ID NOs:11-19. In addition, the skilled person will recognize that nucleic acid molecules comprising the complement of SEQ ID NOs:1-9 or SEQ ID NOs:11-19 can also be determined from SEQ ID NOs:1-9 and SEQ ID NOs:11-19, respectively. The sequences of beta-COP and/or a fragment thereof can be targeted by an interfering RNA of the invention which may cause cessation of feeding, growth, development and/or reproduction of a pest insect, and eventually results in the death of the pest insect. In some aspects of the invention, an interfering RNA molecule of the invention comprises, consists essentially of or consists of any of SEQ ID NOs:20-37, or a complement thereof.

In some embodiments, the invention encompasses an RNA encoded by a sequence comprising, consisting essentially of or consisting of any of SEQ ID NOs:1-9, any at least 19 nucleotide fragment of any of SEQ ID NOs:1-9, the complement of any at least 19 nucleotide fragment of any one of SEQ ID NOs:1-9, or a sequence that hybridizes under stringent conditions with any of the aforementioned sequences, wherein the RNA post transcriptionally silences an essential gene in a plant pest organism.

It is known in the art that dsRNA molecules that are not perfectly complementary to a target sequence (for example, having only 95% identity to the target gene) are effective to control coleopteran pests (see, for example, Narva et al., U.S. Pat. No. 9,012,722). The invention provides an interfering RNA molecule comprising at least one dsRNA, where the dsRNA is a region of double-stranded RNA comprising annealed at least partially complementary strands, a sense strand and an antisense strand. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides which is at least partially complementary to a target nucleotide sequence within an insect pest target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:20-37, or the complement thereof; (ii) comprises, consists essentially of or consists of at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:20-37, or the complement thereof; (iii) comprises, consists essentially of or consists of at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of SEQ ID NOs:20-37, and the complements thereof, wherein the interfering RNA molecule has insecticidal activity against at least a coleopteran insect pest. In some embodiments, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata.*

In some embodiments, the interfering RNA molecule comprises at least two dsRNAs, wherein each dsRNA comprises a sequence of nucleotides which is at least partially complementary to a target nucleotide sequence within the target gene. In some embodiments the target gene comprises, consists essentially of or consists of any one of SEQ ID NOs:1-9. In some embodiments, each of the dsRNAs comprise a different sequence of nucleotides which is complementary to a different target nucleotide sequence within the target gene. In other embodiments, each of the dsRNAs comprise a different sequence of nucleotides which is complementary to a target nucleotide sequence within two different target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24, 25, 26, 27, 28, or 29) to at least about 300 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises, consists essentially of or consists of an antisense strand that is complementary to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NOs:20-37, or the complement thereof. In other embodiments, the portion of dsRNA comprises, consists essentially of or consists of at least from 19, 20 or 21 consecutive nucleotides to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of any one of SEQ ID NOs:20-37, or the complement thereof.

In other embodiments, an interfering RNA molecule of the invention comprises a dsRNA which comprises, consists essentially of or consists of any 21-mer subsequence of any one of SEQ ID NOs:29-37 consisting of N to N+20 nucleotides, or any complement thereof. For example, an interfering RNA molecule of the invention comprises a dsRNA which comprises, consist essentially of or consists of any 21-mer subsequence of SEQ ID NO:29, wherein N is nucleotide 1 to nucleotide 2863 of SEQ ID NO:29, or any complement thereof. In other words, the portion of the mRNA that is targeted comprises any of the 2,863 21 consecutive nucleotide subsequences i.e. 21-mers, of SEQ ID NO:29, or any of their complementing sequences.

In still other embodiments, the interfering RNA molecule of the invention comprises a dsRNA which comprises, consists essentially of or consists of SEQ ID NO:20-37, or the complement thereof.

In other embodiments, the interfering RNA molecule comprises the antisense strand of a dsRNA of the invention which comprises, consists essentially of or consists of the antisense of any one of nucleotide sequences SEQ ID NOs:20-37. The nucleotide sequence of the antisense strand of a dsRNA of the invention can have one nucleotide at either the 3' or 5' end deleted or can have up to six nucleotides added at the 3' end, the 5' end or both, in any combination to achieve an antisense strand consisting essentially of any 19-mer, any 20-mer, or any 21-mer nucleotide sequence, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of this invention, the antisense strand of the dsRNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele1" *Acta Pharmacol. Sin.* 29:211-216 (2008); Schwarz et al. "Asymmetry in the assembly of the RNAi enzyme complex" *Cell* 115:199-208 (2003)).

In some embodiments of the invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn, rice, wheat or soybean.

The invention encompasses a nucleic acid construct comprising an interfering RNA of the invention. The invention further encompasses a nucleic acid molecule encoding at least one interfering RNA molecule of the invention. The invention further encompasses a nucleic acid construct comprising at least one interfering RNA molecule of the invention or comprising a nucleic acid molecule encoding the at least one interfering RNA molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 21-mer subsequences of any one of SEQ ID NOs:29-37, or any complement thereof, operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer, 20-mer, or 21-mer subsequences of the antisense of any one of SEQ ID NOs:29-37. The use of artificial plant microRNAs to deliver a nucleotide sequence of interest (e.g. an artificial miRNA; siRNA/siRNA*) into a plant is known in the art (see, e.g., Schwab et al. 2006. The Plant Cell 18:1121-1133). In the invention, the artificial microRNAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

Plant pest insects that are targets of the present invention include those insects in the Orders Coleoptera (beetles), Lepidoptera (moths, butterflies), Diptera (flies), Protura, Collembola (springtails), Diplura, Microcoryphia (jumping bristletails), Thysanura (bristletails, silverfish), Ephemeroptera (mayflies), Odonata (dragonflies, damselflies), Orthoptera (grasshoppers, crickets, katydids), Phasmatodea (walkingsticks), Grylloblattodea (rock crawlers), Mantophasmatodea, Dermaptera (earwigs), Plecoptera (stoneflies), Embioptera (web spinners), Zoraptera, Isoptera (termites), Mantodea (mantids), Blattodea (cockroaches), Hemiptera (true bugs, cicadas, leafhoppers, aphids, scales), Thysanoptera (thrips), Psocoptera (book and bark lice), Phthiraptera (lice; including but not limited to suborders Amblycera, Ischnocera and Anoplura), Neuroptera (lacewings, owlflies, mantispids, antlions), Hymenoptera (bees, ants, wasps), *Trichoptera* (caddisflies), Siphonaptera (fleas), Mecoptera (scorpion flies), Strepsiptera (twisted-winged parasites). In some embodiments, a target insect is in the Order Coleoptera.

In some embodiments, target coleopteran insect pests of the invention are *Meligethes* species, *Sitophilus* species, *Ceuthorrhynchus* species, *Rhyzoperta* species, *Phyllotreta* species, *Psylliodes* species and/or *Leptinotarsa* species.

In other embodiments, insect pests that are targets of the invention are selected from the group consisting *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata.*

In some embodiments of the invention, the insect pest is a *Meligethes* species and the target sequence is a beta-COP that comprises, consists essentially of or consists of SEQ ID NO:1, the complement of SEQ ID NO:1, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:1, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:1, or a sequence that hybridizes under stringent conditions with any of the aforementioned sequences; wherein the RNA is effective in inhibiting expression of the target beta-COP sequence in a *Meligethes* species. In other embodiments, the insect pest species is *Meligethes aeneus* and the target sequence comprises, consists essentially of or consists of SEQ ID NO:11 or the complement thereof. In other embodiments, the target sequence comprises, consists essentially of or consists of SEQ ID NO:29, the complement of SEQ ID NO:29, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:29 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:29. In other embodiments, the RNA that effectively inhibits expression of the target beta-COP sequence in *Meligethes aeneus* comprises, consists essentially of or consists of SEQ ID NO:20 or the complement thereof.

In some embodiments of the invention, the insect pest is a *Sitophilus* species and the target sequence is a beta-COP that comprises, consists essentially of or consists of SEQ ID NO:2, the complement of SEQ ID NO:2, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:2, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:2, or a sequence that hybridizes under stringent conditions with any of the aforementioned sequences; wherein the RNA is effective in inhibiting expression of the target beta-COP sequence in a *Sitophilus* species. In other embodiments, the insect pest species is *Sitophilus oryzae* and the target sequence comprises, consists essentially of or consists of SEQ ID NO:12 or the complement thereof. In other embodiments, the target sequence comprises, consists essentially of or consists of SEQ ID NO:30, the complement of SEQ ID NO:30, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:30 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:30. In other embodiments, the RNA that effectively inhibits expression of the target beta-COP sequence in *Sitophilus oryzae* comprises, consists essentially of or consists of SEQ ID NO:21 or the complement thereof.

In some embodiments of the invention, the insect pest is a *Sitophilus* species and the target sequence is a beta-COP that comprises, consists essentially of or consists of SEQ ID NO:3, the complement of SEQ ID NO:3, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:3, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:3, or a sequence that hybridizes under stringent conditions with any of the aforementioned sequences; wherein the RNA is effective in inhibiting expression of the target beta-COP sequence in a *Sitophilus* species. In other embodiments, the insect pest species is *Sitophilus granarius* and the target sequence comprises, consists essentially of or consists of SEQ ID NO:13 or the complement thereof. In other embodiments, the target sequence comprises, consists essentially of or consists of SEQ ID NO:31, the complement of SEQ ID NO:31, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:31 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:31. In other embodiments, the RNA that effectively inhibits expression of the target beta-COP sequence in *Sitophilus granarius* comprises, consists essentially of or consists of SEQ ID NO:22 or the complement thereof.

In some embodiments of the invention, the insect pest is a *Ceutorhynchus* species and the target sequence is a beta-COP that comprises, consists essentially of or consists of SEQ ID NO:4, the complement of SEQ ID NO:4, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:4, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:4, or a sequence that hybridizes under stringent conditions with any of the aforementioned sequences; wherein the RNA is effective in inhibiting expression of the target beta-COP sequence in a *Ceutorhynchus* species. In other embodiments, the insect pest species is *Ceutorhynchus assimilis* and the target sequence comprises, consists essentially of or consists of SEQ ID NO:14 or the complement thereof. In other embodiments, the target sequence comprises, consists essentially of or consists of SEQ ID NO:32, the complement of SEQ ID NO:32, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:32 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:32. In other embodiments, the RNA that effectively inhibits expression of the target beta-COP sequence in *Ceutorhynchus assimilis* comprises, consists essentially of or consists of SEQ ID NO:23 or the complement thereof.

In some embodiments of the invention, the insect pest is a *Rhyzopertha* species and the target sequence is a beta-COP that comprises, consists essentially of or consists of SEQ ID NO:5, the complement of SEQ ID NO:5, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:5, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:5, or a sequence that hybridizes under stringent conditions with any of the aforementioned sequences; wherein the RNA is effective in inhibiting expression of the target beta-COP sequence in a *Rhyzopertha* species. In other embodiments, the insect pest species is *Rhyzopertha dominica* and the target sequence comprises, consists essentially of or consists of SEQ ID NO:15 or the complement thereof. In other embodiments, the target sequence comprises, consists essentially of or consists of SEQ ID NO:33, the complement of SEQ ID NO:33, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:33 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:33. In other embodiments, the RNA that effectively inhibits expression of the target beta-COP sequence in *Rhyzopertha dominica* comprises, consists essentially of or consists of SEQ ID NO:24 or the complement thereof.

In some embodiments of the invention, the insect pest is a *Phyllotreta* species and the target sequence is a beta-COP that comprises, consists essentially of or consists of SEQ ID NO:6, the complement of SEQ ID NO:6, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:6, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:6, or a sequence that hybridizes under stringent conditions with any of the aforementioned sequences; wherein the RNA is effective in inhibiting expression of the target beta-COP sequence in a *Phyllotreta* species. In other embodiments, the insect pest species is *Phyllotreta nemorum* and the target sequence comprises, consists essentially of or consists of SEQ ID NO:16 or the complement thereof. In other embodiments, the target sequence comprises, consists essentially of or consists of SEQ ID NO:34, the complement of SEQ ID NO:34, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:34 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:34. In other embodiments, the RNA that effectively inhibits expression of the target beta-COP sequence in *Phyllotreta nemorum* comprises, consists essentially of or consists of SEQ ID NO:25 or the complement thereof.

In some embodiments of the invention, the insect pest is a *Psylliodes* species and the target sequence is a beta-COP that comprises, consists essentially of or consists of SEQ ID NO:7, the complement of SEQ ID NO:7, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:7, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:7, or a sequence that hybridizes under stringent conditions with any of the aforementioned sequences; wherein the RNA is effective in inhibiting expression of the target beta-COP sequence in a *Psylliodes* species. In other embodiments, the insect pest species is *Psylliodes chrysocephala* and the target sequence comprises, consists essentially of or consists of SEQ ID NO:17 or the complement thereof. In other embodiments, the target sequence comprises, consists essentially of or consists of SEQ ID NO:35, the complement of SEQ ID NO:35, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:35 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:35.

In other embodiments, the RNA that effectively inhibits expression of the target beta-COP sequence in *Psylliodes chrysocephala* comprises, consists essentially of or consists of SEQ ID NO:26 or the complement thereof.

In some embodiments of the invention, the insect pest is a *Phyllotreta* species and the target sequence is a beta-COP that comprises, consists essentially of or consists of SEQ ID NO:8, the complement of SEQ ID NO:8, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:8, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:8, or a sequence that hybridizes under stringent conditions with any of the aforementioned sequences; wherein the RNA is effective in inhibiting expression of the target beta-COP sequence in a *Phyllotreta* species. In other embodiments, the insect pest species is *Phyllotreta striolata* and the target sequence comprises, consists essentially of or consists of SEQ ID NO:18 or the complement thereof. In other embodiments, the target sequence comprises, consists essentially of or consists of SEQ ID NO:36, the complement of SEQ ID NO:36, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:36 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:36. In other embodiments, the RNA that effectively inhibits expression of the target beta-COP sequence in *Phyllotreta striolata* comprises, consists essentially of or consists of SEQ ID NO:27 or the complement thereof.

In some embodiments of the invention, the insect pest is a *Leptinotarsa* species and the target sequence is a beta-COP that comprises, consists essentially of or consists of SEQ ID NO:9, the complement of SEQ ID NO:9, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:9, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:9, or a sequence that hybridizes under stringent conditions with any of the aforementioned sequences; wherein the RNA is effective in inhibiting expression of the target beta-COP sequence in a *Leptinotarsa* species. In other embodiments, the insect pest species is *Leptinotarsa decemlineata* and the target sequence comprises, consists essentially of or consists of SEQ ID NO:19 or the complement thereof. In other embodiments, the target sequence comprises, consists essentially of or consists of SEQ ID NO:37, the complement of SEQ ID NO:37, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:37 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:37. In other embodiments, the RNA that effectively inhibits expression of the target beta-COP sequence in *Leptinotarsa decemlineata* comprises, consists essentially of or consists of SEQ ID NO:28 or the complement thereof.

In some embodiments, the invention encompasses a composition comprising one or more or two or more of the interfering RNA molecules of the invention. In some embodiments, the interfering RNA molecules are present on the same nucleic acid construct, on different nucleic acid constructs, or any combination thereof. For example, one interfering RNA molecule of the invention may be present on a nucleic acid construct, and a second interfering RNA molecule of the invention may be present on the same nucleic acid construct or on a separate, second nucleic acid construct. The second interfering RNA molecule of the invention may be to the same target gene or to a different target gene.

In some embodiments, the invention encompasses a composition comprising an interfering RNA molecule which comprises at least one dsRNA wherein the dsRNA is a region of double-stranded RNA comprising annealed complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 consecutive nucleotides which is at least partially complementary to a target nucleotide sequence within a target gene comprising, consisting essentially of or consisting of any one of SEQ ID NOs:1-9. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37 or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of any one of SEQ ID NOs:20-37, and the complements thereof.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises a RNA molecule comprising an antisense strand consisting essentially of a nucleotide sequence comprising at least a 19 consecutive nucleotide fragment of any one of SEQ ID NOs:29-37, and in some embodiments may further comprise an RNA molecule comprising an antisense strand consisting essentially of a second nucleotide sequence comprising at least a 19 consecutive nucleotide fragment of any one of SEQ ID NOs:29-37; and in some embodiments may further comprise an RNA molecule comprising an antisense strand consisting essentially of a third nucleotide sequence comprising at least a 19 consecutive nucleotide fragment of the antisense any one of SEQ ID NOs:29-37, and in some embodiments may further comprise an RNA molecule comprising an antisense strand consisting essentially of a fourth nucleotide sequence comprising at least a 19 consecutive nucleotide fragment of the antisense any one of SEQ ID NOs:29-37, and in some embodiments may further comprise an RNA molecule comprising an antisense strand consisting essentially of a fifth nucleotide sequence comprising at least a 19 consecutive nucleotide fragment of the antisense of SEQ ID NO:29-37, and in some embodiments may further comprise an RNA molecule comprising an antisense strand consisting essentially of a sixth nucleotide sequence comprising at least a 19 consecutive nucleotide fragment of the antisense of any one of SEQ ID NOs:29-37, and in some embodiments may further comprise an RNA molecule comprising an antisense strand consisting essentially of a seventh nucleotide sequence comprising at least a 19 consecutive nucleotide fragment of the antisense of any one of SEQ ID NOs:29-37. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of an insect pest gene described herein, comprising at least one interfering RNA of the invention and/or the DNA encoding it and/or the expression construct of the invention and/or a cell (active or inactivated) expressing the RNA molecule of the invention and an agriculturally acceptable carrier. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

In some embodiments, an acceptable agricultural carrier is a formulation useful for topically applying the insecticidal composition comprising the interfering RNA molecule to a plant or seed. In some embodiments, the formulation may be in any form suitable for application to a plant, a seed or directly to a target insect pest. In one aspect, the formulation may be in solid form (powder, pellet, or a bait), liquid form, or gel form. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of: Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In order to apply an active ingredient to insects and/or crops of useful plants as required by the methods of the invention said active ingredient may be used in pure form or, more typically, formulated into a composition which includes, in addition to said active ingredient, a suitable inert diluent or carrier and optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). SFAs include non-ionic, cationic and/or anionic surfactants, as well as surfactant mixtures. Thus in further embodiments according to any aspect of the invention mentioned hereinbefore, the active ingredient will be in the form of a composition additionally comprising an agriculturally acceptable carrier or diluent.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the active ingredient.

Dustable powders (DP) may be prepared by mixing the active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing the active ingredient with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredient and one or more powdered solid diluents or carriers, or from pre-formed blank granules by absorbing the active ingredient (or a solution thereof, in a suitable agent) in a porous granular material (such as pumice, attapulgite clays, fuller's earth, kieselguhr, diatomaceous earths or ground corn cobs) or by adsorbing the active ingredient (or a solution thereof, in a suitable agent) on to a hardcore material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the active ingredient in water or an organic solvent, such as a ketone, alcohol or glycol ether. These solutions may contain a surface active agent (for example to improve water dilution or prevent crystallisation in a spray tank). Emulsifiable concentrates (EC) or oil-in-water emulsions (EW) may be prepared by dissolving the active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 15060 and SOLVESSO 200; SOLVESSO is a Registered TradeMark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as C8-C10 fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining the active ingredient either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EW s include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SF As, to produce spontaneously a thermodynamically stable isotropic liquid formulation. The active ingredient is present initially in either the water or the solvent/SPA blend. Suitable solvents for use in MEs include those hereinbefore described for use in ECs or in EWs. A ME may be either an oil-in-water or a water-in-oil system (which system is present may be determined by conductivity measurements) and may be suitable for mixing water-soluble and oil-soluble pesticides in the same formulation. A ME is suitable for dilution into water, either remaining as a microemulsion or forming a conventional oil-in-water emulsion.

Suspension concentrates (SC) may comprise aqueous or non-aqueous suspensions of finely divided insoluble solid particles of the active ingredient. SCs may be prepared by ball or bead milling the solid active ingredient in a suitable medium, optionally with one or more dispersing agents, to produce a fine particle suspension of the compound. One or more wetting agents may be included in the composition and a suspending agent may be included to reduce the rate at which the particles settle. Alternatively, the active ingredient may be dry milled and added to water, containing agents hereinbefore described, to produce the desired end product.

Aerosol formulations comprise the active ingredient and a suitable propellant (for example n-butane). Active ingredients may also be dissolved or dispersed in a suitable medium (for example water or a water miscible liquid, such as n-propanol) to provide compositions for use in non-pressurised, hand-actuated spray pumps. The active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredient and, optionally, a carrier or diluent therefor. The polymeric shell may be produced by either an interfacial polycondensation reaction or by a coacervation procedure. The compositions may provide for controlled release of the compound of the active ingredient. Active ingredients may also be formulated in a biodegradable polymeric matrix to provide a slow, controlled release of the compound. A composition may include one or more additives to improve the biological performance of the composition (for example by improving wetting, retention or distribution on surfaces; resistance to rain on treated surfaces; or uptake or mobility of the active ingredient). Such additives include surface active agents, spray additives based on oils, for example certain mineral oils, natural plant oils (such as soy bean and rape seed oil) and/or modified plant oils (e.g. esterified plant oils), and blends of these with other bio-enhancing adjuvants (ingredients which may aid or modify the action of the active ingredient. Where the active ingredient described herein is employed in methods of protecting crops of useful plants, methods of enhancing/maintaining yield and/or methods of increasing/maintaining pollination in crops of useful plants, it is preferred that said active ingredient (or compositions containing such active ingredient) is applied to the crop of useful plants at the flower-bud stage. In particular for crops of useful plants wherein said plants have yellow flowers, (e.g. oilseed rape, mustard etc.) it is preferred that the application occurs at the green to yellow bud stage.

In some embodiments, the acceptable agricultural carrier is a transgenic organism expressing an interfering RNA of the invention. In some embodiments the transgenic organism may be a living or a non-living transgenic bacteria expressing the interfering RNA of the invention that when fed upon by a target insect pest causes the target insect pest to stop feeding, growing or reproducing or causing death of the target insect pest. In some embodiments the target insect pest is selected from the group consisting of *Meligethes aeneus, Sitophilus oryzae, Sitophilus granaries, Ceutorhynchnus assimilis, Rhyzopertha dominica, Phyllotreta nemorum, Psylliodes chrysocephala, Phyllotreta striolata* and *Leptinotarsa decemlineata.*

In other embodiments, the transgenic organism is selected from, but not limited to, the group consisting of: yeast, fungi, algae, plants, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*, Symbiotic fungi, such as *Trichoderma* and *Gliocladium* are also possible hosts for expression of the inventive interfering RNA molecule for the same purpose.

In some embodiments, the invention encompasses transgenic plants, or parts thereof, comprising an interfering RNA molecule, a nucleic acid construct, a chimeric nucleic acid molecule, a artificial plant microRNA precursor molecule and/or a composition of the invention, wherein the transgenic plant has enhanced resistance to at least a coleopteran insect compared to a control plant. The invention further encompasses transgenic seed of the transgenic plants of the invention, wherein the transgenic seed comprises an interfering RNA molecule, a nucleic acid construct, a chimeric nucleic acid molecule, an artificial plant microRNA precursor molecule and/or a composition of the invention.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. In addition, promoters functional in plastids can be used. In some embodiments of the invention, inducible promoters can be used. In further aspects, the nucleotide sequences of the invention can be operably associated with a promoter that is wound inducible or inducible by pest or pathogen infection (e.g., a insect or nematode plant pest)

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or npII, which confers resistance to kanamycin, G418, and the like (Potrykus et a. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988). *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan: and/or a nucleotide sequence encoding hph that confers resistance to hygromycin. One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823: 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinothricin acetyltransferase (pat), which provides tolerance to the herbicide phosphinothricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U.S. Pat. Nos. 5,849,320 and 5,876,739, herein incorporated by reference.

Where both the insecticide or insecticidal seed coating and the transgenic plant or seed of the invention are active against the same target insect, for example at least a coleopteran insect pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of at least a coleopteran insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorpyrifos), Fortress® (chlorethoxyfos), Mocap® (ethoprop), Thimet® (phorate), AAstar® (phorate, flucythrinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The compositions of the invention can also be combined with other biological control agents to enhance control of at least a coleopteran insect population. Thus, the invention provides a method of enhancing control of at least a coleopteran insect population by providing a transgenic plant that produces an interfering RNA of the invention and further comprises a polynucleotide that encodes a second insecticidal agent. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the transgenic plant may produce an interfering RNA of the invention and a second insecticidal agent which is derived from sources other than *B. thuringiensis*. The second insecticidal agent can be an agent selected from the group comprising a patatin, a protease, a protease inhibitor, a chitinase, a urease, an alpha-amylase inhibitor, a pore-forming protein, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporus* insecticidal protein, a *Lysinibacillus sphaericus* insecticidal protein, a *Chromobacterium* spp. insecticidal protein, a *Yersinia entomophaga* insecticidal protein, a *Paenibacillus popilliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabdus, Serratia*, or *Yersinia*. In other embodiments. the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporus* or BinA and BinB from *L. sphaericus*. In still other embodiments, the insecticidal protein may be engineered or may be a hybrid or chimera of any of the preceding insecticidal proteins.

In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is a transgenic corn plant.

The invention further encompasses a method of controlling at least a coleopteran pest insect comprising contacting the insect with a nucleic acid molecule that is or is capable of producing an interfering RNA molecule of the invention for inhibiting expression of a beta-COP target gene in the insect thereby controlling the coleopteran insect. In some embodiments, the coleopteran insect is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata*. In some embodiments, the target gene comprises, consists essentially of or consists of a coding sequence (i) having at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:1-9, or a complement thereof; (ii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one SEQ ID NOs:1-9, or a complement thereof, (iii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:1-9, or a complement thereof. In some embodiments the target gene coding sequence comprises, consists essentially of or consists of any one of SEQ ID NOs:1-9, or a complement thereof, or (iv) can hybridize under stringent conditions to a polynucleotide selected from the group consisting of any one of SEQ ID NOs:1-9, and the complements thereof. In other embodiments, the interfering RNA molecule of the invention is complementary to a portion of a mRNA polynucleotide transcribable from the pest insect target genes described herein. In other embodiments, the mRNA comprises, consists essentially of or consists of any one of SEQ ID NOs:29-37.

In some embodiments of the method of controlling a coleopteran insect pest, the interfering RNA molecule of the invention comprises at least one dsRNA, wherein the dsRNA is a region of double-stranded RNA comprising annealed complementary strands, one strand of which comprises a sequence of at least 19 consecutive nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; or (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of any one of SEQ ID NOs:20-37, and the complements thereof. In other embodiments, the interfering RNA comprises, consists essentially of or consists of any one of SEQ ID NOs:20-28, and the target gene is a beta-COP in an insect pest selected from the group consisting of *Meligethes aeneus, Sitophilus oryzae, Sitophilus granaries, Ceutorhynchus assimilis. Rhyzopertha dominica, Phyllotreta nemorum, Psylliodes chrysocephala, Phyllotreta striolata* and *Leptinotarsa decemlineata.*

In other embodiments of the method of controlling a coleopteran insect pest, the contacting comprises (a) planting a transgenic seed capable of producing a transgenic plant that expresses the nucleic acid molecule, wherein the insect feeds on the transgenic plant, or part thereof; or (b) applying a composition comprising the nucleic acid molecule to a seed or plant, or part thereof, wherein the insect feeds on the seed, the plant, or a part thereof.

In still other embodiments, the invention encompasses a method of producing a transgenic plant cell having toxicity to a coleopteran insect of the invention, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the insect compared to a control plant cell. In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to at least coleopteran insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of identifying a beta-COP gene in an insect pest for interfering RNA targeting, said method comprising the steps of: a) isolating nucleic acid from an insect pest; b) amplifying an orthologous beta-COP target gene from the nucleic acid with a pair of primers comprising nucleotide sequences selected from SEQ ID NOs:38-55: c) identifying a sequence of an orthologous beta-COP target gene; d) producing a dsRNA molecule, wherein the dsRNA molecule comprises a sense strand and an antisense strand, wherein a nucleotide sequence of the antisense strand is complementary to a portion of a mRNA polynucleotide transcribable from the insect pest beta-COP gene that comprises a beta-COP coding sequence, and e) testing the dsRNA molecule of step d) for insecticidal activity against the insect pest. In some embodiments, the insect pest is a coleopteran insect pest. In other embodiments, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Leptinotarsa decemlineata.*

EXAMPLES

The invention will be further described by reference to the following detailed examples. These examples are provided for the purposes of illustration only, and are not intended to be limiting unless otherwise specified.

Example 1. Identification of Target Genes

For each species, a library of assembled contigs was constructed. These sequences were compared via BLAST to known lethal genes and alleles, which were identified based on published disclosures including those in the website wormbase (wormbase.org) and Boutros et al (2004, Science 303: 832-835). From this analysis, several target genes were identified. Contigs with matches to target genes with an expect value of 1e-10 or lower were considered potentially significant matches. Full-length beta-COP genes were identified in each of the species.

dsRNA Synthesis of Target Genes dsRNAs of those targets were produced on an 96 w automated library synthesis platform. All the dsRNA samples tested were designed automatically using Primer3, a primer design tool, to synthetize a dsRNA fragment of around 600-800 bp based on the coding sequence of each target gene. Smaller fragments were designed if the size of the coding sequence did not allow a 600 bp fragment. The PCR template for dsRNA synthesis was amplified from cDNA that was reverse transcribed using standard methods from mRNA isolated from whole insects. Primers (corresponding to SEQ ID Nos:38-55) containing T7 promoter sequences were used to amplify the fragment of the genes, followed by in vitro transcription, using standard methods, to synthesize dsRNA. The RNA was further purified following standard methods and the pellet was re-suspended in double distilled water. The concentration and quality of each dsRNA sample was analyzed on a Dropsense96 spectrophotometer (Trinean).

Example 2. Activity of dsRNA Molecules Targeting Beta-COP

In Vitro Bio-Assay *Meligethes aeneus*

A dsRNA molecule comprising SEQ ID NO:20 which corresponds to SEQ ID NO:11, targeting beta-COP (SEQ ID NO:1) was tested for toxicity against pollen beetle, *Melighethes aeneus* in laboratory bioassays. In vitro bioassays were performed in 3-cm Petri dishes, using an RNA-treated artificial diet method. Briefly, synthesized dsRNA molecules were diluted to the appropriate concentration in a sucrose solution. Samples containing dsRNA and sucrose are heated up to 60° C. An agarose solution was heated till boiling and added to the dsRNA dilutions leading to final concentrations of 5% sucrose and 0.5% agarose. The agarose solution containing the dsRNA was divided over three Petri dishes, at a final dose of 67 μg of dsRNA per Petri dish. Ten to twelve adults were added to each Petri dish resulting in 30 to 36 adults per treatment. Petri dishes were stored at 25° C. with a 16 hour: 8 hour light:dark photoperiod. Mortality was recorded at 1 or 2, 3, 4, 6, 7, 8 days post-infestation. DsRNA of non-target GFP was used as a negative control and dsRNA designed to target an ubiquitin gene of *Meligethes aeneus* was used as a positive control.

In Vitro Bioassay *Sitophilus oryzae*

A dsRNA molecule comprising SEQ ID NO:21 which corresponds to SEQ ID NO:12, targeting beta-COP (SEQ ID NO:2) was tested for toxicity against the rice weevil, *Sitophilus oryzae* in laboratory bioassays. In vitro bioassays were performed in 6-well plates, using an RNA-treated artificial diet method. Briefly, synthesized dsRNA molecules were diluted to the appropriate concentration and mixed with Bio flour in a final 9:1 ratio (v/w). The suspension was continuously mixed, divided over three wells at a final dose of 80 μg of dsRNA per well and left to dry. Eight adults were added to each well, resulting in 24 adults per treatment. The plates were stored at 25° C. with a 16 hour: 8 hour light:dark photoperiod. Mortality was recorded at 3, 5, 7, 10, 12 and 13 days post-set up. DsRNA of non-target GFP was used as a negative control and dsRNA designed to target an ubiquitin gene of *Sitophilus oryzae* was used as a positive control.

In Vitro Bioassay *Sitophilus granarius*

A dsRNA molecule comprising SEQ ID NO:22 which corresponds to SEQ ID NO:13, targeting beta-COP (SEQ ID NO:3) was tested for toxicity against the grain weevil, *Sitophilus granarius* in laboratory bioassays. In vitro bioassays are performed in 6-well plates using an RNA-treated artificial diet method. Briefly, synthesized dsRNA molecules are diluted to the appropriate concentration in a sucrose solution. Samples containing dsRNA and sucrose are heated up to 60° C. An agarose solution is heated till boiling and added to the dsRNA dilutions, leading to final concentrations of 5% sucrose and 0.5% agarose. The agarose solution containing the dsRNA is divided over three wells, at a final dose of 80 μg of dsRNA per well. Eight adults are added to each well resulting in 24 adults per treatment. Each plate is stored at 25° C. with a 16 hour: 8 hour light:dark photoperiod. Mortality was recorded at 3, 5, 7, 10, 12 and 14 days post-infestation. DsRNA of non-target GFP is used as a negative control and dsRNA designed to target an ubiquitin gene of *Sitophilus granarius* is used as a positive control.

In Vitro Bioassay *Ceutorhynchus assimilis*

A dsRNA molecule comprising SEQ ID NO:23 which corresponds to SEQ ID NO:14, targeting beta-COP (SEQ ID NO:4) is tested for toxicity against the cabbage seedpod weevil, *Ceutorhynchus assimilis* in laboratory bioassays. In vitro bioassays are performed in 6-well plates using an RNA-treated artificial diet method. Briefly, synthesized dsRNA molecules are diluted to the appropriate concentration in a sucrose solution. Samples containing dsRNA and sucrose are heated up to 60° C. An agarose solution is heated till boiling and added to the dsRNA dilutions, leading to final concentrations of 5% sucrose and 0.5% agarose. The agarose solution containing the dsRNA is divided over three wells, at a final dose of 80 μg of dsRNA per well. Eight adults are added to each well resulting in 24 adults per treatment. Plates are stored at 25° C. with a 16 hour: 8 hour light:dark photoperiod. Mortality is recorded at 2, 3, 4, 5, 7, and 10 days post-infestation. DsRNA of non-target GFP is used as a negative control and dsRNA designed to target an ubiquitin gene of *Ceutorhynchus assimilis* is used as a positive control. The dsRNA is found to be active against *Ceutorhynchus assimilis.*

In Vitro Bioassay *Rhyzopertha dominica*

A dsRNA molecule comprising SEQ ID NO:24 which corresponds to SEQ ID NO:15, targeting beta-COP (SEQ ID NO:5) was tested for toxicity against lesser grain borer, *Rhyzopertha dominica*, in laboratory bioassays. In vitro bioassays were performed in 24-well plates using an RNA-treated artificial diet method. Briefly, synthesized dsRNA molecules were diluted to the appropriate concentration in a flour suspension. The suspension containing the dsRNA was divided over three wells at a final dose of 100 μg dsRNA per well and left to dry. Ten adults were added to each well resulting in 30 adults per treatment. Plates were sealed and stored at 25° C. with a 16 hour; 8 hour light:dark photoperiod. Mortality was recorded at 1, 2, 5, 6, 7, 8, 9, 12 days post-infestation. DsRNA of non-target GFP was used as a negative control and dsRNA designed to target an ubiquitin gene of *Rhyzoperta dominica* was used as a positive control.

In Vitro Bioassay *Phyllotreta Nemorum*

A dsRNA molecule comprising SEQ ID NO:25 which corresponds to SEQ ID NO:16 targeting beta-COP (SEQ ID NO:6), is tested for toxicity against flea beetles, *Phyllotreta nemorum* in laboratory bioassays. In vitro bioassays are performed in 3 cm Petri dishes using an RNA-treated artificial diet method. Briefly, synthesized dsRNA molecules are diluted to the appropriate concentration in a sucrose solution. Samples containing dsRNA and sucrose is heated up to 60° C. An agarose solution is heated till boiling and added to the dsRNA dilutions, leading to final concentrations of 5% sucrose and 0.5% agarose. The agarose solution containing the dsRNA is divided over three Petri dishes at a final dose of 67 μg dsRNA per Petri dish. Ten to twelve adults are added to each Petri dish resulting in 30 to 36 adults per treatment. Petri dishes are stored at 25° C. with a 16 hour: 8 hour light:dark photoperiod. Mortality is recorded at 1, 2, 5, 6, 7, 8, 9 days post-infestation. DsRNA of non-target GFP is used as a negative control and dsRNA designed to target an ubiquitin gene of *Phyllotreta nemorum* is used as a positive control. The dsRNA is found to be active against *Phyllotreta nemorum.*

In Vitro Bioassay *Psylliodes chrysocephala*

A dsRNA molecule comprising SEQ ID NO:26 which corresponds to SEQ ID NO:17 targeting beta-COP (SEQ ID NO:7), was tested for toxicity against flea beetles, *Psylliodes chrysocephala* in laboratory bioassays. In vitro bioassays were performed in 3 cm Petri dishes using an RNA-treated artificial diet method. Briefly, synthesized dsRNA molecules were diluted to the appropriate concentration in a sucrose solution. Samples containing dsRNA and sucrose was heated up to 60° C. An agarose solution was heated till boiling and added to the dsRNA dilutions, leading to final concentrations of 5% sucrose and 0.5% agarose. The agarose solution containing the dsRNA was divided over three Petri dishes at a final dose of 67 μg dsRNA per Petri dish. Ten to twelve adults were added to each Petri dish resulting in 30 to 36 adults per treatment. Petri dishes were stored at 25° C. with a 16 hour; 8 hour light:dark photoperiod. Mortality was recorded at 1, 2, 5, 6, 7, 8, 9 days post-infestation. DsRNA of non-target GFP was used as a negative control and dsRNA designed to target an ubiquitin gene of *Psylliodes chrysocephala* was used as a positive control.

In Vitro Bioassay *Phyllotreta striolata*

A dsRNA molecule comprising SEQ ID NO:27 which corresponds to SEQ ID NO:18, targeting beta-COP (SEQ ID NO:8) was tested for toxicity against flea beetle, *Phyllotreta striolata*, in laboratory bioassays. In vitro bioassays were performed in 20 ml plastic cups, using RNA-treated leaf disks. Briefly, synthesized dsRNA molecules were diluted to the appropriate concentration and applied to canola leaf discs (5 mm diameter), coating the top surface with a final dose of 20 ng/mm2. Leaf disks were placed in cups containing ten adults per cup. Adult beetles were fed fresh leaf discs, coated with dsRNA, every second day, for a period of two weeks. The cups were stored at 25° C. with a 16 hour: 8 hour light:dark photoperiod and mortality was recorded every second day. dsRNA of non-target GFP was used as a negative control and dsRNA designed to target an ubiquitin gene of *Phyllotreta striolata* was used as a positive control.

In Vitro Bioassay *Leptinotarsa decemlineata*

A dsRNA molecule comprising SEQ ID NO:28 which corresponds to SEQ ID NO:19, targeting beta-COP (SEQ ID NO:9) was tested for toxicity against the Colorado potato beetle, *Leptinotarsa decemlineata* in laboratory bioassays. In vitro bioassays were performed in 48-well plates using an RNA-treated artificial diet method. Briefly, molten artificial diet, was poured into each well and allowed to solidify. DsRNA molecules were diluted to appropriate concentration. 20 μl of the dsRNA solution was added to the surface of the diet resulting in a final overlay concentration of 1 μg, 0.1 μg, 0.01 μg and 0.001 μg dsRNA per well. One L2 larva was placed in each well and 24 larvae were tested per treatment. Plate were stored at 25° C. with a 16 hour: 8 hour light:dark photoperiod. Mortality was recorded at 3, 4, 5, 6, 7 and 10 days post-infestation. dsRNA of non-target GFP was used as a negative control and dsRNA designed to target an ubiquitin gene of *Leptinotarsa decemlineata* was used as a positive control.

Results of the bioassays described above, shown in Table 1, demonstrate that Beta-COP is an effective target to control coleopteran insect pests *Meligethes aeneus, Sitophilus oryzae, Sitophilus granaries, Rhyzopertha dominica, Psylliodes chrysocephala, Phyllotreta striolata* and *Leptinotarsa decemlineata*.

TABLE 1.

Activity of dsRNA targeting Beta-COP in coleopteran pests.

| Target ID: beta-COP, CG6223 | Insect Pest | Sequence ID | % Mortality |
|---|---|---|---|
| Nitidulidae | *Meligethes aeneus* | SEQ ID NO: 1 | 81.6 |
| | *Sitophilus myzae* | SEQ ID NO: 2 | 100 |
| Curculionidae | *Sitophilus granarius* | SEQ ID NO: 3 | 100 |
| Bostrichidae | *Rhyzopertha dominica* | SEQ ID NO: 5 | 76 |
| | *Psylliodes chrysocephala* | SEQ ID NO: 7 | 95.3 |
| Chrysomelidae | *Phyllotreta striolata* | SEQ ID NO: 8 | 72.2 |
| | *Leptinotarsa decemlineata* | SEQ ID NO: 9 | 90.5 |

Example 3. Expression of an Interfering RNA Molecule Comprising a dsRNA in Plants Vector Construction for *Agrobacterium*-Mediated Transformation A binary vector comprising at least one expression cassette designed to produce a hairpin RNA (hpRNA) comprising a promoter operably linked to a sense strand of a target nucleic acid sequence, an intron functioning as a loop sequence, a corresponding antisense strand, and a terminator. The binary vector may also comprise a second cassette between the left and right T-DNA borders, designed to express a selectable marker for use in selection of transformed plant cells. The binary vector may also contain selectable markers for selection of transformed bacteria, for example transformed *Agrobacterium tumefaciens* bacterial cells which contain the binary vector.

Canola Transformation

Canola plant material can be suitably transformed and fertile plants regenerated by many methods which are well known to one of skill in the art. For example, transgenic *Brassica napus* plants can be produced by *Agrobacterium*-mediated transformation following the methods taught by Wang et al (2003. Plant Cell Reports 22: 274-281). Transgenic plants may then be assayed for resistance to insect species by a feeding assay, and/or they may be grown to maturity for T1 seed production. T1 plants may be grown and may also be assayed for resistance to insect species by a feeding assay.

Rice Transformation

Rice plant material can be suitably transformed and fertile plants regenerated by many methods which are well known to one of skill in the art. For example, transgenic rice plants can be produced by *Agrobacterium*-mediated transformation following the methods taught by Toki et al (1997. Plant Molecular Biology Reporter 15 (1): 16-21). Transgenic plants may then be assayed for resistance to insect species by a feeding assay, and/or they may be grown to maturity for T1 seed production. T1 plants may be grown and may also be assayed for resistance to insect species by a feeding assay.

Wheat Transformation

Wheat plant material can be suitably transformed and fertile plants regenerated by many methods which are well known to one of skill in the art. For example, transgenic wheat plants can be produced by biolistic bombardment following the methods taught by Chang et al (U.S. Pat. No. 5,955,362). Transgenic plants may then be assayed for resistance to insect species by a feeding assay, and/or they may be grown to maturity for T1 seed production. T1 plants may be grown and may also be assayed for resistance to insect species by a feeding assay.

Transgenic Canola Assay

A binary vector containing an expression cassette comprising a sequence encoding a hairpin RNA, comprising a sequence of SEQ ID NO:11, targeting beta-COP (SEQ ID NO:1), is transformed into *Agrobacterium tumefaciens* using standard molecular biology techniques known to those skilled in the art. To prepare the Agrobacteria for transformation cells are cultured in liquid YPC media at 28° C. and 220 rpm overnight.

The vector described above is transformed into canola. Following transformation, selection, and regeneration, plants are tested for the presence of the hairpin dsRNA comprising the RNA sequence encoded by SEQ ID NO:11. Positive plants from the PCR assay are transferred to the greenhouse and tested for resistance to at least *Meligethes aeneus*.

Transgenic plants producing interfering RNA and control, non-transgenic plants of the same genetic background are infested with *Meligethes aeneus* larvae for a period of days. Plants are then examined for feeding damage and for the presence of *Meligethes aeneus* insects.

Example 4. Producing dsRNA Molecules by Bacterial Expression

This example describes producing dsRNA molecules engineered against identified insect pests using a bacterial expression system.

Hairpin cassettes are engineered for selected insect target genes as described above. The hairpin cassette comprises a T7 promoter operably linked to an antisense sequence of the target, further linked at the 3' end to a nucleic acid sequence which is capable of forming a loop structure, further linked at the 3' end to the corresponding sense sequence of the target, operably linked at the 3' end to a T7 terminator sequence. The hairpin cassette is introduced into a bacterial expression vector, for example pGCP295, via appropriate restriction sites, for example BamHI and NotI. The vector is then introduced into an *Escherichia coli* strain, for example, HT115(DE3)GA01, via electroporation using standard methods, and transformants are selected using kanamycin selection.

The bacteria containing the targeted dsRNA expression vector plasmid are grown in defined medium to a specific optical density and induced by addition of IPTG for a specific time period following standard methods and routine optimization. After induction, the bacteria are harvested by centrifugation, and the produced dsRNA molecules are collected.

Example 5. Activity of dsRNA Molecules in a Spray Application Assay

This example describes testing of a sub-set of the identified target dsRNAs of the invention for biological activity against stink bugs when applied as a spray. The production of bacterial lysate is described above.

Plants, e.g. canola plants, are sprayed with a about 15% sucrose solution containing bacterial lysate expressing non-targeting GFP dsRNA and beta-COP dsRNA molecules from the expression vectors described above. Test insects are then placed on each sprayed plant. Plants are placed in a box coated with fluon PTFE to prevent insect escape and stored in a rearing chamber (26° C., 65% RH, with 16:8 hours l:d). Photographs are taken on a daily basis to record plant health. Insect survival rate is recorded 3 to 14 days post exposure to the sprayed plant. These experiments are performed using at least *Meligethes aeneus*. A dsRNA of non-target GFP is used as a negative control and a dsRNA designed against a known a lethal gene is used as positive control. Percent mortality of the insect on day 14 is recorded.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A double stranded RNA (dsRNA) molecule comprising a sense strand and an antisense strand, wherein a nucleotide sequence of the antisense strand consists of a sequence that is complementary to a mRNA polynucleotide transcribable from a portion of a coleopteran insect beta coatomer (beta-COP) gene that consists of from 600 to 787 consecutive nucleotides of SEQ ID NO: 17, and wherein the dsRNA molecule is toxic to at least a coleopteran insect pest, and wherein the dsRNA molecule has at least about 95% mortality in *Psylliodes chrysocephala* within 10 days of exposure to the dsRNA molecule.

2. The dsRNA of claim 1, wherein the antisense strand consists of the A complement of i) of from 200 to 787 consecutive nucleotides of SEQ ID NO: 26; or ii) SEQ ID NO: 26.

3. The dsRNA molecule of claim 1, wherein the nucleotide sequence of the sense strand is substantially or fully complementary to the nucleotide sequence of the antisense strand.

4. The dsRNA molecule of claim 1, wherein the dsRNA is a short hairpin RNA (shRNA) molecule.

5. The dsRNA molecule of claim 1, wherein the coleopteran insect pest is selected from the group consisting of *Melighethes aeneus, Sitophilus oryzae, Sitophilus granaries, Ceutorhynchus assimilis, Rhyzopertha dominica, Phyllotreta nemorum, Phyllotreta striolata, Psylliodes chrysocephala* and *Leptinotarsa decemlineata.*

6. A nucleic acid molecule encoding the dsRNA molecule of claim 1.

7. A recombinant vector comprising a regulatory sequence operably linked to the nucleic acid molecule of claim 6.

8. A bacteria that comprises the recombinant vector of claim 7.

9. An insecticidal composition comprising the dsRNA of claim 1 and an acceptable agricultural carrier.

10. The insecticidal composition of claim 9, comprising at least a second insecticidal agent.

11. The insecticidal composition of claim 10, wherein the second insecticidal agent is a biological agent or a chemical agent.

12. The insecticidal composition of claim 11, wherein i) the biological agent is a *Bacillus thuringiensis* insecticidal protein, a *Bacillus cereus* insecticidal protein, a *Xenorhabdus* spp. insecticidal protein, a *Photorhabdus* spp. insecticidal protein, a *Brevibacillus laterosporus* insecticidal protein, a *Lysinibacillus sphaericus* insecticidal protein, a *Chromobacterium* spp. insecticidal protein, a *Yersinia entomophaga* insecticidal protein, a *Paenibacillus popilliae* insecticidal protein, or a *Clostridium* spp. insecticidal protein, a patatin, a protease, a protease inhibitor, a urease, an alpha-amylase inhibitor, a pore-forming protein, a lectin, an engineered antibody or antibody fragment, or a chitinase; or ii) the chemical agent is a carbamate, a pyrethroid, an organophosphate, a friprole, a neonicotinoid, an organochloride, a nereistoxin, or a combination thereof.

13. A method of controlling at least a coleopteran insect pest comprising contacting the coleopteran insect pest with a nucleic acid molecule that is or is capable of producing the dsRNA molecule of claim 1 for inhibiting expression of a beta-COP target gene in the coleopteran insect pest, and contacting the coleopteran insect pest with at least a second insecticidal agent for controlling a coleopteran insect pest.

14. The method of claim 13, wherein the second insecticidal agent is a biological agent or a chemical agent, optionally wherein i) the biological agent is a *Bacillus thuringiensis* insecticidal protein, a *Bacillus cereus* insecticidal protein, a *Xenorhabdus* spp. insecticidal protein, a *Photorhabdus* spp. insecticidal protein, a *Brevibacillus laterosporus* insecticidal protein, a *Lysinibacillus sphaericus* insecticidal protein, a *Chromobacterium* spp. insecticidal protein, a *Yersinia entomophaga* insecticidal protein, a *Paenibacillus popilliae* insecticidal protein, or a *Clostridium* spp. insecticidal protein, a patatin, a protease, a protease inhibitor, a urease, an alpha-amylase inhibitor, a pore-forming protein, a lectin, an engineered antibody or antibody fragment, or a chitinase; or ii) the chemical agent is a carbamate, a pyrethroid, an organophosphate, a friprole, a neonicotinoid, an organochloride, a nereistoxin, or a combination thereof.

15. A double stranded RNA (dsRNA) molecule comprising a sense strand and an antisense strand, wherein a nucleotide sequence of the antisense strand consists of a sequence that is complementary to a mRNA polynucleotide transcribable from a portion of a coleopteran insect beta coatomer (beta-COP) gene, wherein the portion of the coleopteran insect beta coatomer (beta-COP) gene A consists of from 600 to 787 consecutive nucleotides and wherein the dsRNA molecule is toxic to at least a coleopteran insect pest, and wherein the dsRNA molecule has a length of 787 base pairs.

* * * * *

SEQUENCE LISTING

```
<160> NUMBER OF SEQ ID NOS: 55

<210> SEQ ID NO 1
<211> LENGTH: 2883
<212> TYPE: DNA
<213> ORGANISM: Meligethes aeneus

<400> SEQUENCE: 1

atgactgctg tagaacagcc ctgttacact ttaattaatt tacccaccga ttcggagcct     60
tacaatgaaa tgcagcttaa gcaggattta gaaaaaggag aaattaagca aaaggttgaa    120
gccctcaaga aaattataca catgattttg gcaggtgaaa gattaccccc aggcttttta    180
atgttaataa taaggtatgt tttaccactg caagaccatt tagccaaaaa gttgttactt    240
atattttggg aaattgttcc caaaactaca caagatggaa aattattaca agaaatgata    300
ttggtttgtg atgcttaccg taaggattta caacatccca atgaattttt acgcggttct    360
acattaagat ttttgtgtaa attaaaagaa cctgagcttt tggaacccct aatgccatcc    420
atacgttctt gcttggagca tagacactct tatgtacgta gaaatgctgt acttgctatt    480
ttcactattt acagaaactt tgaattctta attcctgatg cacctgagtt aatatcaact    540
tacttggaag gtgaacatga tatgtcttgt aaacgtaatg ctttcctaat gttgttacat    600
gctgatcagg atagagctct atcgtacttg gctaattgtt tggatcaagt aaatactttt    660
ggggatattt tgcagttggt tatagtggag ttgatttata aggtttgcca ttcaaatcct    720
gcagaaagat caagatttat taggtgtatt tataatttgt tgaattcaag tagccctgct    780
gtaagatatg aggctgcagg tactttggtt accttgtcaa atgctcccac tgcaattaaa    840
gctgctgcga gttgttacat tgaattgatt attaaggaaa gtgataataa tgttaaacta    900
attgttttgg atcgattgat tgctctaaaa gaacatccaa gtcatgaaag agttctacaa    960
gatctagtga tggacattct gagagttcta tcaagccctg acttggaggt tagaaaaaaa   1020
acgttaaatt tagctttgga tttggtttcg tcaagaaata ttgaagaaat ggttttggtt   1080
ttgaaaaaag aagtttccaa aactcatgat gtagagcatg aggatacagg aaagtaccga   1140
caacttttgg tcaggacttt acatacatgc tccattaagt ttcctgatat tgctgccact   1200
gtaataccag tattggtgga attcttgtct gacacaaatg agttagctgc cactgatgtt   1260
ttggtgtttg taagagaggc tatacagaag tttgataatc tacaaccact tattattgag   1320
aaacttttgg aatgcttccg cgacataaaa tccgtaaaag ttcacagggc ggccttgtgg   1380
attttgggag agtatgctac tgaagtgaac gatattgagt ccgttcttaa agaaattaat   1440
tcggctcttg gtgaaggtcc tcttctggag gcagaacaac ggttggtgtc tggtgattcc   1500
gatgagggat cgaagccggc tatggctcaa aataccgcac catcagcctc ccttgttacc   1560
```

```
tctgatggta cttatgcaac acaatctgct ttcaacacag tgcaaaaaga taaagaagtt   1620
aagaggccac cactaagaca gtacctaatg gacggtgatt tctttattgg agctgctttg   1680
gcctcaaccc taaccaaact ggctctaaga tatgcaaaat tgaatgagca tctaaaagca   1740
aacaggtttg atgccgaaat tatgttaatt atggcaggaa ttatacattt gggaaagtca   1800
ggcttgccta caaaaccaat caccaacgac gacaaagacc atattctatt ttgtcttcgc   1860
gttatatcgg accgtagtcc caccatcatc gaagtattcg tgcaattgtg tcgtaacgcg   1920
ctaaacgata tgctcatcgc taaagagatt gaagaagcct cgactcaaaa agctaaagaa   1980
aaagccggta acttgatcca aaccgatgat ccaattaatt tcatgcaatt agaaagtgat   2040
agatcagggg aattgggcga aaacgttttc gagatgtcgt tgaatcaggc cgtaataggc   2100
ggccgtggtc agggtcaaga ttctaataca ggggtaaata agttaaataa ggtaacacaa   2160
ttgaccggtt tttcggatcc agtttacgca gaagcatacg tacacgtaaa ccaatacgat   2220
atagttctgg atgtacttat tgttaaccaa acaaacgata ccctacaaaa ttgcacccta   2280
gaattagcaa cactgggcga cttaaaactt gtggaaaaac ctcaacccgt agtacttgca   2340
cctcgcgact tctgcaatat taaagctaac gtaaaagtgg cctcaaccga aaatggtatt   2400
atattcggta atatcgttta cgatgtgacc ggtgccgctt cagatcgcaa tgttgttgtt   2460
ctcaacgaca ttcatatcga tattatggac tacattgtac cagcttcttg caacgattct   2520
gaattcatga ggatgtgggc ggaattcgaa tgggaaaaca aagtaaccgt taacaccccc   2580
attacggacc ttgcggaata ccttaaacat ctcattaaaa gtaccaatat gaaatgcttg   2640
actccggaaa aggctttgtc cggtcagtgt ggatttatgg cggccaacat gtatgctaaa   2700
tctatttttg gagaggatgc tttggctaat ttaagtattg agaagccttt taataagcct   2760
gatgccccag tggctggaca tattcgtata agagctaaga gtcagggaat ggctttaagt   2820
cttggagata agatcaatat gacccaaaaa ggtctgcaca acagcaaagt aaccgcgggt   2880
taa                                                                 2883
```

```
<210> SEQ ID NO 2
<211> LENGTH: 2877
<212> TYPE: DNA
<213> ORGANISM: Sitophilus oryzae

<400> SEQUENCE: 2

atgacgagcg tcgaacagcc ctgttacacc ctgatcaatg tgtcttcgga tacagagccc     60
tacaacgaga tgcatttgaa aagcgatctc gagaagggcg atacagacca aaaggtcgaa    120
gcattaaaga agattattcg aatgatcttg gcaggcgaaa gattacctcc aggtttcctc    180
atgatgatta ttcgctacgt tcttcctttg caagaccaca cagctaaaaa actcctactt    240
atattctggg aaattgtccc taaaactaca cccgatggca agcttctgca agaaatgatt    300
ctagtttgtg acgcttacag aaaagactta caacacccta acgagttctt acgcggttcc    360
accttgagat ttctctgcaa actgaaggaa ccagagcttc tcgaaccttt aatgccttca    420
ataagggctt gtttagaaca cagacatagc tacgttagga gaaacgcagt gcttgctatt    480
tttacaatat acaggaactt tgagtttctt atacccgatg ctccagaact gatatcaact    540
tatttagatg gagaacagga tatgtcttgt aaaagaaatg cgtttttgat gttgctgcat    600
gccgatcagg atagggcact gtcttatttg agttcttgtc tcgatcaagt cacttctttt    660
ggagatattc ttcagttagt tatagtggag ttgatataca aggtgtgcca ttcaaatccc    720
```

```
acagaaagat caagatttat caggtgtatt tataatttac ttaactcaag tagtgcggct    780
gttaggtatg aagctgcagg tactcttata actctatcca gtgcacctac agctattaaa    840
gctgctgctt catgttatat tgatcttatc atcaaggaaa gcgataataa tgttaaactt    900
attgtcctgg acaaactagt aactctaggg gaacatccaa actataacag agttcttcag    960
gacttggtaa tggatatttt aagagtttta tctagtccgg acctggaagt aagaagaaaa   1020
accttaaatc tagccatgga gctggttaat tccaggaata ttgaagaaat ggtcttgttc   1080
ttgaagaaag aagtatcaaa aacccttgac tctgagcatg aagatacagg aaaataccga   1140
caactcttgg tcaggacctt gcattcttgc tgtataaagt ttcctgatgt tgctgccaca   1200
gttataccga ttttggtaga gtttttgtca gataataacg agctagctgc cgcagatgtg   1260
ttagtttttg taagagaggc catacaaaag ttcgaggcac ttagaccact tattattgag   1320
aaacttcttg aagctttcaa ggatataaaa tcagtgaaag tccatagggc tgccctgtgg   1380
attcttggag agtatgctac atcggttgct gatatagagt cagtcataaa agaggtgaca   1440
tatacattgg gcgagggttc ttttgttgta gccgaacaca gactcaatca aggcgaagta   1500
gacgaaaaag aaatagaaaa cataggaaac ggtcctgtcg tgactactct agtgacgtca   1560
gacggtacct acgccactca gtcggcgttt aacactgttc agaaatcgaa aaaagaaaga   1620
ccgcctttaa ggcagtacct tatggacgga gatttcttca ttggagcttc tctggcttca   1680
actttgacca aactggcttt gagatttggt cagctggttt ctgcagaaag aaccaacaga   1740
tttgacgcag aggtcatgtt gattatggcg gggatactgc atttgggcca atcaggcttg   1800
ccaaccaaat cgatcacaaa cgacgacagg gaccatatct tgctctgcct gaaggtagtc   1860
tctgacagat cgcctgtcat agttcagatc tttaccgact attgtaggaa ggccctgaac   1920
gacatgctat tggccaaaga gcgcgaggaa gcgtcaaatc agaaggccaa agaaaaaaca   1980
gggcacaaaa ttcaaacgga cgacccgatc aatttcattc agttggagac tgataagggt   2040
ggcgaattgg gggaaaatgt attcgaaacg tcgttatctc aagctctgat tggaggaaga   2100
gccgcaggcg gggacactgg tttgggtcca aataaactgg acaaagtcac ccaactcaca   2160
ggtttctcag atccggtata ttcagaggcg tacgttcacg tgaatcagta cgatatcgtc   2220
ttggacgtac tgatcgtgaa ccagaccaac gacacgttgc aaaattgtac tttagagctg   2280
gcaacgttgg gcgacttgaa gttggtcgaa aaacctcaac ccgtggttct ggcgcctaaa   2340
gatttctgta acatcaaagc aaacgttaag gttgcttcca ctgaaaacgg tattattttc   2400
ggcaacattg tctatgacgt caccggtgcc gcgtctgaca gaaatgtggt ggttttgaat   2460
gatatacaca tcgatataat ggactacata gtaccagcga gttgtaccga cacagagttt   2520
atgcgcatgt gggcggagtt tgagtgggag aacaaggtaa ctgtcaacac gtcgttgaca   2580
gatctgaacg aatacttaaa acacctgatc aagagtacca acatgaagtg tctgacgccg   2640
gaaaaagcgc tgtcaggcca gtgcggtttc atggctgcca acatgtacgc caaatctatt   2700
tttggtgaag acgctttggc caatttgagt atagaaaaac ccttcaacaa accagaagct   2760
cctgtacagg gtcatatcag gataagggcc aaaagtcagg gtatggcttt gagtttagga   2820
gataaaataa acagtagtca gaaggctgga cttcaaacaa aagttgcggc ggcataa      2877
```

```
<210> SEQ ID NO 3
<211> LENGTH: 1716
<212> TYPE: DNA
<213> ORGANISM: Sitophilus granarius

<400> SEQUENCE: 3
```

```
cattcttgtt gtataaaatt tcctgatgtc gctgcagcgg ttataccaat tttggtagag     60

tttttatcag ataataatga gctagccgct gctgatgtgt tagtttttgt aagagaagcc    120

atacaaaaat ttgaggcact tagaccaatt attattgaga aacttcttga agcgttcaag    180

gatataaaat cggtaaaagt acatagagct gcactgtgga ttcttggaga atatgctacg    240

tcagttgctg atatagagtc ggtcataaaa gaggtgacgt atacattggg tgaaggatcc    300

cttgtcgtgg ctgaacacag gctcaaccaa ggcgaggtgg acgaaaaaca aatagaaaat    360

atcgggaacg gtccagtcgt gactactcta gtgacgtcag acggtactta cgctactcaa    420

tcggccttta acaccgttca gaaatcgaaa aaagaaaggc cgcccttaag gcagtacctt    480

atggatggag atttctttat tggagccgct ctggcttcga ctttgaccaa actggctttg    540

agatttggtc agctagtgtc accggaaaga acaaacagat ttgacgcgga agtcatgttg    600

attatggcgg gaatactgca tttaggccaa tcaggcttgc caaccaaatc gatcacgaac    660

gacgacaggg accacatctt gctctgtttg aaggtggtgt ctgacagatc gcccgtcatt    720

gttcagatct tcaccgacta ctgtcgaaag gccttaaacg acatgctatt ggccaaagag    780

cgcgaggaag cgtccaatca gaaggccaaa gaaaaaacag ggcacaaaat tcaaacggac    840

gatccgatca atttcattca gctggagact gataagggtg gagaattggg cgagaacgta    900

ttcgaaacgt cgttatcgca agcgctgatt gggggaagag ccgcgggcgg ggacactggt    960

ttaggtccaa ataaactgga caaagtcact caactcacag gtttctcgga tccggtatat   1020

tcagaggcgt acgtgcacgt gaatcagtac gacatcgttt tggacgtact gatcgtgaat   1080

cagaccaacg acacgttgca gaactgtacg ttagagctgg caacgttggg cgacctgaaa   1140

ttggtggaaa aacctcaacc cgttgttttg gcccctaaag atttctgcaa tattaaagca   1200

aacgttaagg ttgcttccac tgaaaatggt attatattcg gcaacattgt ctatgacgtc   1260

accggcgccg cgtctgacag aaatgtcgtc gttttgaacg acatacacat agacattatg   1320

gactacattg tgccagccag ttgcaccgac acagagttta tgcgcatgtg ggcggaattt   1380

gagtgggaga acaaggtaac tgtcaacaca tccttgacag atctaaacga atacctaaaa   1440

cacctgatca agagtaccaa catgaagtgt ctgaccccag aaaaagccct gtcgggccag   1500

tgcggcttca tggctgccaa catgtacgct aagtctattt ttggtgaaga tgcgttagcc   1560

aatttgagta tagagaaacc ctttaacaaa ccagaagctc ctgtacaggg tcatatcagg   1620

ataagggcca aaagtcaggg tatggctttg agtttaggag ataaaataaa taatagccaa   1680

aaggctggac ttcaaactaa agttgccgca gcataa                              1716
```

```
<210> SEQ ID NO 4
<211> LENGTH: 2880
<212> TYPE: DNA
<213> ORGANISM: Ceuthorrhynchus assimilis

<400> SEQUENCE: 4

atgacgaacg tagaacagcc ctgttacacc ctaatcaacg tgtcttccga tacagagccc     60

tacaatgaaa tgcatctaaa aagtgattta gaaaaaggtg acacagacca aaaaatagaa    120

gccctcaaaa agactattcg catgatacta gcaggagaac gcctaccgcc aggtttcctg    180

atgataatta ttcgttacgt acttccttta caagaccata ccgccaaaaa attattacta    240

atttttgggg aaattgttcc taaaacaaca ccagatggta aacttttaca agaaatgatt    300

ctggtttgcg atgcttacag aaaagatttg caacatccaa acgaattttt gagagggtca    360
```

-continued

```
acactgaggt ttttgtgtaa acttaaggaa cctgaattac tggaaccact tatgccatca    420
atcagagctt gtttggagca cagacacagc tatgtcagaa gaaatgctgt tttagcaata    480
tttactattt atcgcaattt tgaatttcta attcctgacg ctccagaact tatttcaaat    540
tacttagata gcgaacaaga tatgtcgtgc aaaaggaacg cctttttaat gttgctacat    600
gctgatcaag acagagcttt atcttatttg agctcttgct tagatcaagt tacttctttt    660
ggagatattt tacaactggt tattgtagaa ctgatttata aggtttgtca taccaaccca    720
tcagaaagat ccagattcat ccgttgcata tacaatttgc taaactctag tagtgccgca    780
gtaagatatg aagctgcagg cactcttatt acattatcca gtgcccctac tgctatcaga    840
gcggcggctt cttgttacat tgatttaatt gtcaaggaga gcgacaataa tgttaaacta    900
attgttttgg ataagttggt tgcccttggc gaacatccaa cctataacag ggttttgcag    960
gatctcgtta tggatatact aagagttttg agtagtcctg atttagaagt gagaaggaaa   1020
actttaaatt tagccatgga actagtgaat tctagaaata ttgaggaaac tgttttgttt   1080
ttgaaaaaag aagtttcaaa aactttagat tctgaacatg aagatacagg caaatatagg   1140
caacttcttg taagaacttt gcattcctgc tgtattaaat ttcctgatgt tgctgccaca   1200
gtgattccag ttttggtgga atttttgtct gataccaatg agttagctgc tgctgatgtt   1260
ttggtgttta tcagagaagc tatacagaaa tttgaaaatt tgcgagcact tattattgag   1320
aaacttcttg attcatttaa ggatattaaa tctgtcaaag tacatagagc cgccttgtgg   1380
attttgggtg aatatgccac atctgttcct gatattgaag cagttataaa agagataaca   1440
cttactctag gagaaggctc actagttgca gcagaaaatc gccttaacca aggagatgtt   1500
gcggaaaata aaccagaagg agcaagcagt agtggccctg ttgttactac tctagtaact   1560
tcagatggca catacgctac tcaatctgca ttcaattctg tccaaaagtc cacaaaagaa   1620
aaacgtccac ctcttcgcca atatatgatc gatggggatt tctttattgg ggcttcttta   1680
gcttcaacaa taactaaaat agctttaaga tatggcaacc ttgtgacacc tgaaaaacgt   1740
aaccgatttg atgctgaaat tatgcttatt atgagcggcg ttattcattt gggacaatca   1800
ggtctaccaa caaaaccaat caccaacgac gaccgcgatc atattttatt ttgtctcaga   1860
gttttatctg acaggtcacc aatcataatt gaaatattta ctgaatattg cagaaaggct   1920
cttaacgata tgctattggc caaggaatta gaggaagcta gcaaccagaa agctaaagaa   1980
aaaaaaggca ctaaaatcca tacagacgat ccaatcaatt tcttgcaact tgaaacagac   2040
aaaggtggag aattgggaga aaatgtcttt gaaacctctc tgtcacaggc attggttggt   2100
ggacgaactg gcggcgggga tggtttaagt accaataaat taaacaaagt tacgcaactc   2160
acaggtttct cagatcctgt ttatgctgaa gcctatgttc acgttaacca atacgatatt   2220
gtattggatg ttttaattgt aaatcaaact aatgacactt tgcaaaattg cacgttagaa   2280
ttggcaacgc tgggtgattt aaaactggta gagaaaccac aacctgtagt gttggcacct   2340
aaagattttt gcaatattaa agcaaatgtt aaggttgcat ctacagaaaa tggtataatt   2400
tttggtaaca ttgtatacga catcactgga gccgcctcag atagaaatgt tgtagtctta   2460
aatgacatac atattgacat tatggactat atagtgccag ccaactgtaa cgatactgaa   2520
tttatgcgaa tgtgggctga atttgaatgg gaaaacaagg ttaccgtgaa tactcagcta   2580
acagacctaa acgaatacct aaaacaccta attaaaagca caaacatgaa atgtttgact   2640
ccggaaaaag cattatctgg tcagtgtgga ttcatggctg ccaatatgta tgcaaaatct   2700
atttttggag aagatgcttt ggctaatttg agtattgaga agccgtttaa caagccagat   2760
```

```
gctcctgttc agggacatat taggataaga gccaaaagtc aaggtatggc gttaagcttg   2820

ggagacaaaa tcaacagcag ccaaaaggct caacaacaaa acaaagttgt tgctgcataa   2880


<210> SEQ ID NO 5
<211> LENGTH: 1005
<212> TYPE: DNA
<213> ORGANISM: Rhyzoperta dominica

<400> SEQUENCE: 5

ctatctattg tgaaagtatt tgtgcaagaa tgtcgaaatg ccctgaacga aatgcttctt     60

gctgaagaag aggaggagca aacaacaaag aaggctaaag aaaaagccgg gaagaaaatt    120

caagctgatg atccaattag ttttatgcag ctgcaatctg ataagtcagg tgaattaggt    180

gacaacatct ttgaaacctc actctcacaa gcacttgctg gtggccgtcc tggtacagct    240

gacctagcag cttccatcag caaattaaac aaagtaacac aattaactgg cttctcagat    300

ccagtgtatg ctgaagctta tgtacatgta aatcagtatg atattgtgct ggatgttttg    360

attgtgaatc agactaatga tactttacaa aactgcacct tggaactggc gacattaggt    420

gatctaaaac ttgttgagaa accgcagcct gttgtgcttg cacctaaaga tttctgtaat    480

ataaaggcaa atgttaaggt tgcatctaca gaaaatggta tcatttttgg aaacattgtg    540

tatgatatta ctggtgctgc ctcagataga aatgttgttg ttttgaatga catacacatt    600

gacattatgg attacattgt tcctgcatct tgtaatgata ctgaatttag acagatgtgg    660

gcagagtttg aatgggaaaa taaggtttct gtgagcacca cattgacaga tttagcagaa    720

tatctcaaac tcttgattaa gagtacaaat atgaagtgct taaccccaga gaaggccctt    780

tctggacagt gtggatttat ggcagccaat atgtatgcca agtctatatt tggtgaagat    840

gccttggcta atttgagtat tgagaagcca tttaataaac ccgatgctcc tgtcagtggt    900

catataagaa taagggctaa aagtcagggc atggctctca gcctgggaga taagatcaat    960

atgactcaaa aaggacagca aacaaaggtg gttgctgctg cttaa                   1005


<210> SEQ ID NO 6
<211> LENGTH: 2871
<212> TYPE: DNA
<213> ORGANISM: Phyllotreta nemorum

<400> SEQUENCE: 6

atgacggcgg tcgagcagcc ctgttacact ttaattaatc ttccgaccga ttcggagcct     60

tacaatgaaa tgcaattgaa aatggacctc gaaaagggcg aagtcaaagt aaagataagg    120

gctttggaaa gaatcataca catgatattg gcaggcgaga gattgcccaa cggattcctg    180

atgacaatca tacgaaacgt tttgccccta caagatcacc tggccaagaa acttttgctc    240

attttttggg aaatcgtgcc gaaaaccacc cccgacggta aattactgca ggaaatgatc    300

ctagtctgtg acgcctacag aaaggacctg cagcacccca acgaattttt gaggggctcc    360

acattgagat tcctatgcaa gctgaaggag cccgagctgt tggagcctct gatgcccagc    420

attcgaattt gcctcgaaca caggcacagc tacgttcgaa ggaatgccgt tctggccatt    480

tttacgatat acaagaattt cgaattcctc attccagacg cccctgaatt gatttctact    540

tatctagacg gcgagcaaga tatgtcttgt aaaagaaacg ctttccttat gcttttgcat    600

gccgaccaag atcgagccct cacttaccta tccaattgct tagatcaagt ggcttctttt    660

ggggatattc tacagttggt tattgttgaa ttgatataca aagtgtgcca ctccaacccc    720
```

```
gccgagagat ccagattcat tcgatgcata tacaatctat taaattcgag cagtcctgct    780
gttcggtacg aggccgccgg tactctgatt actctgtcca gcgctccgac agccatcaaa    840
gccgccgcta gttgttacat cgaattgatc attaaagaga gcgacaacaa cgtcaaattg    900
atcgttttgg atagattgat cgccttaaag gagcatccca gccacgagag agtcctgcag    960
gatttggtta tggatatatt gagagtttta tcggctcctg atttggaagt gcgaaagaaa   1020
acacttaatt tagcgctgga attggtgtcc tctcgtaacg tcgaagaaat ggtgtttgtg   1080
ctgaagaaag aggtgtctaa aactgtggac agcgaacaag aagacaccgg gaaatatagg   1140
caattgttgg tcagaacatt gcactcctgc tgcatcaaat tccccgatat agctgcaacg   1200
gtcattcctg ttttgatgga attcctgtcc gatagcaacg aattagcggc cactgatgtg   1260
ttgctatttt tgagggaagc catacagaaa ttcgataatt tagagccgct cattatcgaa   1320
aaattattgg agacattcaa agacatcaaa tctgtgaaag tacatcgagc tgctctttgg   1380
atactgggcg aatacgccac gtcgactggc gacattgaag ccgtcatcaa ggagatcgtt   1440
caaaccttgg gcgaatgccc attgttggag actgagcaga agagtatatc tggtaacacg   1500
gatgaaagtg cgccggttca tgcaccagct ggggctacca ctttggttac ttcagatgga   1560
acgtacgcca ctcagtctgc tttcaacgtg gccagcaaat cgacgaaaga gaagagacct   1620
ccattgaggc aatacctgat ggacggagat ttcttcattg ccgcttctct ggcttctact   1680
ttaaccaaac tggctttgag gtatggcgaa aacgtttccg cttccgatag gaataaattc   1740
gacgccgaag ttatgctcat tatggctggc attttgcatc taggcaaatc aggtttgccc   1800
gtaaaaccga taaccaacga cgacaacgac cacatcctct tctgcctgcg cgtgctatcc   1860
gatcgaacgg accccgtcat ccaagtattc tcgagcctct gccgcaacgc cctcaacgac   1920
atgctgctag ccaaggaaac cgaagaggcg accgatcaaa aatcccgcga aaaatcccga   1980
gccgccgtcc aaaccgacga cgccatcacc ttcgtgcagc tggagtccga tcgaagcggc   2040
gagctcggcg aaaacatgtt tgaaacctcc ctctcgcagg ccctcatggg cggcaagacg   2100
gcccaatccg actcgaccat cggctcgagc aaactgaaca agatcgccca gctgacgggc   2160
ttctcggatc ccgtctactc cgaagcgtat gtgcacgtca atcagtacga tatcgtgctc   2220
gacgtgctgg tggtgaacca aacgagcgac acgctgcaga actgcacgct cgaattggcg   2280
actttgggcg atttgaagct ggtggagaag ccgcaacccg tcgtgctggc gccgaaggac   2340
ttttgcaaca tcaaggctaa cgtgaaggtg gcttcgaccg agaacggtat catattcggt   2400
aacattgtgt atgacgtgac gggcgccgcg tcggacagga acgtcgtcgt tttgaacgac   2460
attcatatcg acattatgga ttacattgtt ccggcgtcgt gcaccgattc ggagtttatg   2520
aggatgtggg ctgaattcga atgggagaat aaggtgaccg tcaatacgcc gcttacagat   2580
ctcaacgagt acctggagca tttgctaaag agtactaaca tgaagtgtct gacgtctgag   2640
aaggcgctcg gagggcaatg cggcttcatg gccgccaata tgtacgcaaa atcgatcttt   2700
ggggaagacg ccctggcgaa tttgagcatc gagaagccgt tcaacaagcc ggacgcgccc   2760
gtcgccgggc acattagaat tcgtgccaaa agtcagggta tggctttgag tttgggcgac   2820
aaaatcaaca tgacgcagaa agggacgcaa agtaaggtcg ttgccgcgta a            2871
```

<210> SEQ ID NO 7
<211> LENGTH: 2868
<212> TYPE: DNA
<213> ORGANISM: Psylliodes chrysocephala

<400> SEQUENCE: 7

```
atgactgccg ttgaacagtc ttgttatact ttaattaatc taccaactga ttcggagccc     60
tacaatgaaa tgcagctcaa aatggacctc gaaaagggcg aggttaaggt aaaaataaga    120
gcacttgaaa ggattataca catgatatta gctggagaaa gattaccaaa cggattctta    180
atgactatta taaggaatgt ccttcccctt caggatcatt tagctaagaa attacttcta    240
atttttggg aaattgtacc aaaaacttca cctgatggca aattattaca agaaatgatt     300
ttagtgtgtg atgcctacag aaaagatctg caacacccaa acgaatttct tcgaggttct    360
actttaagat tcttatgtaa attaaaagaa ccagaactgc tagaacctct aatggctagt    420
atcagagcct gtttggatca caggcacagt tatgtgcgaa gaaatgcagt tttggctatt    480
tttacaattt atagaaattt tgagttctta attcctgatg cacccgaact tatttctact    540
tatttagatg gtgagcagga tatgtcttgc aagagaaatg cttttctgat gcttttacat    600
gctgatcaag atagagcact gtcttatttg gcaaattgtc tagatcaagt tacatcattt    660
ggagacattc tgcaattggt cattgttgaa ttaatctata aagtttgcca ttcaaatccc    720
acagagaggt caagatttat ccgctgcatt tacaatctat taaattcaag cagtcctgct    780
gtcagatatg aagctgctgg tacacttgta acactttcaa gtgctcccac agcagtaaaa    840
gcagctgcta gttgttatat tgaactaatt atcaaggaaa gtgataataa tgtaaagttg    900
attgtcttgg acagattgat tgcccttaag gaacatccca gccatgaaag ggttttgcaa    960
gatttggtta tggatatatt aagagtgttg caagctcctg acttggaagt tcgcaaaaag   1020
actttaaacc tagcacttga actggtatca tctcgtaata tagaagaaat ggttttggtt   1080
cttaaaaagg aggtatcaaa aaccgtagat agcgagcacg aagatacagg aaaatacagg   1140
cagttacttg ttagaacact tcattcttgt tgtataaaat tcccagatgt agctgtaact   1200
gtcattcctg ttttaatgga atttttgtct gatagtaacg agttagctgc tactgacgtg   1260
ttactatttt tgagagaggc catacagaag tttgataatc tgcaaccact tattattgag   1320
aaacttctag aaacattcaa agatataaaa tctgttaaag tgcatagagc agctctttgg   1380
atattgggag aatatgccac ttctgtctca gacattgaag ctgttattaa agaaattaat   1440
caaaccttag gagaagctcc tctgttggaa actgaacaaa aactaatttc tggagagaca   1500
gacgacacaa ctacagttcc aacaggtgga gctacaactt tggttacttc agatggtact   1560
tacgccactc agtctgcctt taattcagtc agtaaatctt caaaagaaaa acgacctcct   1620
ctgaggcaat atcttatgga tggtgatttt tttataggag cgtccttgac ttctactcta   1680
accaaattag ctttaagata tggtcaaatt gcctcagctg ctgatagaaa taggtttgat   1740
gctgaagtca tgcttattat ggcaggtatc atacatttag gcaaatcagg tttaccgaca   1800
aaaccaataa ccaacgatga caaagaccac atactttttt gcttgcgtgt catctcagac   1860
cgcaccgacc caataataca aattttctct actctgtgtc gatctgctct caatgacatg   1920
ttgatagcga aggaagcgga agaagccacg actcaaaaat ctaaagaaca atccagacac   1980
actatccaaa cagatgacgc tatcagtttc cttcaattag aagcggacaa gagcggcgaa   2040
cttggggaaa atgtattcga aatgtcttta tcacaagcct tggtcggagg tagaggtggc   2100
caaacagact ccctaatcag ttccaataaa ttgaacaaga taacacagtt gactggattt   2160
tcggatcccg tatattcaga agcttacgtc cacgttaatc aatacgatat agttcttgat   2220
gttttaatag tgaatcaaac gaacgacact cttcaaaatt gcacgctgga actggcgacg   2280
ctgggcgatt tgaaactcgt agaaaaacct caacctgtcg tactcgcgcc taaagatttt   2340
```

```
tgtaatatta aggcgaacgt taaggtagct tccacagaaa acggcattat atttggtaat   2400

attgtttacg acgtcaccgg tgccgcttca gatagaaatg tagtggtttt aaatgacatt   2460

catatcgata ttatggatta tattgttccc gcgagctgta cagataccga gtttatgagg   2520

atgtgggcag aatttgaatg ggaaaataag gtcactgtaa atacacctct cacagacctc   2580

gccgattacc ttgaccatct cttgaaaagt acaaacatga aatgtctgac ttccgaaaaa   2640

gcccttagcg gtcaatgcgg atttatggcc gccaatatgt atgccaaatc tattttcgga   2700

gaagacgcgc ttgcaaattt gagcatagaa aagcctttca acaaaccaga tgcaccagtc   2760

gcagggcaca tcaggattag agctaaaagt caaggaatgg ctttgagttt aggtgataaa   2820

ataaatatga cacaaaaagg aactcagagt aaagtagctg ctgcatga             2868
```

<210> SEQ ID NO 8
<211> LENGTH: 2871
<212> TYPE: DNA
<213> ORGANISM: Phyllotreta striolata

<400> SEQUENCE: 8

```
atgacggcgg tcgaacagcc ctgctacact ttaatcaatt tgccgaccga ttcggagcct     60

tacaatgaaa tgcaattgaa aatggatctc gaaaagggcg aaatcaaagt aaagataagg    120

gctttggaaa gaatcataca catgatactg gctggcgaga ggttaccaaa tgggttcctc    180

atgacaatca tacgaaacgt tctgccccta caagatcacc ttgccaagaa gctgttgctc    240

attttttggg aaatcgtgcc gaaaaccacc cccgatggca aattactgca ggaaatgatc    300

ctggtgtgcg acgcctacag aaaggacctg cagcacccca acgaattctt gcgagggtct    360

acattgagat tcctgtgcaa gctaaaggag cccgagctgt tggagcctct gatgcccagc    420

atacgaattt gcctggaaca cagacacagc tacgttcgca ggaatgccgt tctggccatt    480

tttacgatat acaagaattt cgaatttctc attcccgacg cccctgaatt gatttctact    540

tacctagatg gcgaacaaga catgtcttgt aaaaggaacg cttttcttat gctcttgcac    600

gccgatcaag atcgagccct cacttatcta tccaattgtt tagatcaagt cgcttccttc    660

ggggatatcc ttcagttggt tatcgtcgaa ttgatataca aggtgtgcca ctctaacccc    720

accgagagat ccagattcat tcgatgcata tacaatctgt taaattcgag cagtcctgct    780

gttagatacg aagcggcagg tactctcatt actttgtcca gcgctccgac tgctataaaa    840

gccgccgcca gttgttacat cgaattgatc attaaagaga gcgacaacaa cgtcaaattg    900

atcgttttgg atagattgat cgcgttgaag gaacatccga gccacgagag agtcctacag    960

gacttggtta tggatatatt gagagtgtta tcggctcccg atttggaggt gcgaaagaaa   1020

acgcttaatt tagcgctcga attggtgtcc tctcgtaacg tcgaagaaat ggtgtttgtg   1080

ctgaagaagg aggtgtcgaa gaccatggat agcgaacacg aagataccgg gaaatacagg   1140

caactgttgg tcagaacgtt gcattcttgt tgcatcaaat tccccgatat agctgctacg   1200

gtcattcccg ttctaatgga gttcctgtcc gatagcaacg aattggcggc caccgatgtg   1260

ttgctatttc tgagggaagc catacagaaa ttcgataatt tggagccgct cattatcgag   1320

aaattattgg agacattcaa agacatcaaa tcggtgaaag ttcatcgagc cgctctttgg   1380

atattgggcg aatacgccac gtcgactggc gacatcgaag ccgtcatcaa agagatcgtt   1440

cacacgttag gcgaatgccc attgttggag accgagcaaa agattatatc tggtagtact   1500

gaggaaagcg ctccggttca tgcacctgcc ggagcaacca ctttggttac ctcagatgga   1560

acctacgcca ctcaatctgc cttcaacgtg gccagcaaat cgaccaaaga gaagagacct   1620
```

```
ccgttgaggc agtacttaat ggacggagat ttcttcatcg ccgcttctct ggcttctact   1680

ttgaccaaat tggctttgag gtacggcgaa aacgcttcac cttccgatag gaacaaattc   1740

gacgccgaag ttatgctcat catggccgga attctgcacc taggcaaatc aggtttgccg   1800

gtaaaaccga taactaacga cgacaacgac catattctct tctgcctgcg cgtgctgtcc   1860

gatcgcacgg agcccgtggt gcaagtgttc tcgaggctct gccgcaacgc gctcaacgac   1920

atgctgctgg cgaaggagac cgaagaggcg accgatcaga aatcgcgcga gaaatcccga   1980

gcggccgtcc agaccgacga cgccatcacc ttcgtgcaat tggagtccga tcgaagcggc   2040

gagctcggcg agaacgtgtt cgaaacctcc ctgtcgcaag cgctgatggg cggcaaaacg   2100

ggccaatccg attcgagcgt aggatcgagt aaactgaata aaatcgccca gctgacgggt   2160

ttctcggatc ccgtttactc cgaagcgtac gtgcacgtta atcagtacga tatcgtgctc   2220

gatgtgctgg tggtgaacca gacgagcgat acgctgcaga attgcacgtt ggaattggcg   2280

acgctgggcg atttgaagtt ggtggagaag ccgcagcccg tcgtactggc gccgaaggac   2340

ttctgcaata ttaaagctaa cgtgaaggtg gcttcgaccg agaatggtat tatattcggt   2400

aacatcgtgt acgatgtaac cggagccgct tccgacagga acgttgtcgt tttgaacgac   2460

atacacatcg atataatgga ttacattgtt ccggcatctt gcaccgattc ggagtttatg   2520

aggatgtggg ctgaattcga gtgggagaat aaggtgaccg tcaatacgcc gttgacggat   2580

ctcaacgagt acctggagca tctgctgaag agtactaaca tgaagtgcct gacgtcggag   2640

aaggcgctgg gcgggcaatg cggtttcatg gcggctaata tgtacgcgaa atcgatcttt   2700

ggagaggacg ccctggcgaa tttgagcatc gaaaagccgt ttaataagcc ggacgcgccc   2760

gtcgccggtc acattagaat tcgggccaaa agtcagggta tggctttgag tttgggcgac   2820

aagatcaaca tgacgcagaa agggacgcaa agcaaggtgg tcgccgcgta a            2871
```

<210> SEQ ID NO 9
<211> LENGTH: 2868
<212> TYPE: DNA
<213> ORGANISM: Leptinotarsa decemlineata

<400> SEQUENCE: 9

```
atgactacca tggaacagcc ttgttacaca ctcatcaatt ttccgacaga ttctgaacca     60

tataatgaaa tgcaactcaa aacggattta gagaagggcg atgtgaaagt caaaatacga    120

gccttagaaa gaaccattca catgattttg gcaggagaac gcctgccgaa cggtttctta    180

atgacgatta tcaggtatgt tctgccgatt caggatcatt tggccaaaaa gctgttgtta    240

attttttggg aaattgtgcc aaagacctca cctgacggaa aactgctaca ggaaatgatt    300

ctcgtttgtg atgcatatcg gaaagactta caacatccca atgaattcct caggggggtca    360

acgctgaggt ttctttgcaa acttaaggag cctgagttgt tggagcctct gatgccaagc    420

atccggaaat gtttggagca caaacacagt tatgtgagga gaaatgctgt tttagccata    480

ttcaccattt atcgcaattt tgaatttctt atacctgatg ctcctgagct gatttccaac    540

tatctcgatg gagaacaaga catgtcatgc aaacgcaatg cttttctcat gcttctacat    600

gcagatcagg agagggcttt gtcgtattta gcgtcttgcc tggaccaagt tacttcgttc    660

ggtgacatct tacagttggt aattgtggag ttaatataca aagtctgtca cacaaatccc    720

tcagaacgtt cccgattcat cagatgcatt tataacttgc tgaattccag tagtcctgcg    780

gttcgttacg aagccgcagg gactctggta actctatcca gtgccccaac ggccatcaaa    840
```

```
gctgccgcca gctgttacat cgaactcatc atcaaagaaa gtgataacaa cgtgaaactc    900
attgttctgg acagactgat tgcgttgaaa gatcacccca gtcacgagcg agtcttgcaa    960
gacctcgtta tggacatatt aagggttctc tcggccccgg atttggaggt acgcaagaag   1020
actcttagtt tagccatgga gttgatttcg tcacgtaata ttgaagagat ggtactgatt   1080
ttaaagaaag aggtctctaa aacgcttgac agtgaacacg aagacacagg aaagtaccgt   1140
cagttattag ttcgcacgtt gcattcctgc tgtatcaaat ttccagatgt ggccgttacc   1200
gtaattccag tgttgatgga gtttttgtcc gacagtaatg aattggcagc cactgacgta   1260
cttgtgtttg tgagagaggc cgtacagaag tttgagaatt tgcagcctct agttatagag   1320
aaattattgg aaactttcaa ggatatcaaa tctgtaaagg ttcaccgtgc agccctttgg   1380
atattgggag aatatgctac ctctgttagt gatatagaga tggtaatcaa gcaaattaat   1440
caaactttgg gtgattgccc cctcttggaa gcggagcaga gactcgtttc tggagatgca   1500
gaggaaaata tttcaaacat aagtagtacc actacaacgt tggttacatc tgatgggact   1560
tacgctaccc agtcatcttt caatacagtt cacaaatcaa gtaaagaaaa gaggcctcca   1620
cttcgtcaat atttaatgga cggcgatttc tttattggag cctcgctcgc ttccacattg   1680
acaaaattag ctttgcgcta cggaaatctc acttctccct cacaaaggaa tagatttgac   1740
actgaagtca tgttgatcat ggcaggaatt gttcatttgg gaaaatcagg cttgccaacg   1800
aaaccgatca cgaatgacga taaggatcac atcctgttct gtctgagggt tctctccgat   1860
cgtacttccg ccatcattca gatattcaca gagcgctgcc ggctcgctct caatgacatg   1920
cttgtcgcca aagaagcaga agaggcgtcg actctgaaga cgaaagagaa atccggcaat   1980
acgatccaaa cagatgaccc gattagcttc ctccagctag aggccgacaa gaatggagaa   2040
cttggcgaaa acgtatttga gacctcgctg tcgcaagccc tcgtcggtgg aagaggcagc   2100
gcggcagatt ctgccacagg aacaaataag ttgaacaaga taacgcagtt gacaggtttt   2160
tcggatcccg tttattcaga agcttatgtc cacgtcaacc agtacgatat tgtgctggac   2220
gttttgatcg tcaatcaaac taatgatact ctgcaaaatt gtactttgga gctggcgacg   2280
ttgggagatc tgaaacttgt cgaaaaacct cagccagtag ttcttgctcc caaagacttc   2340
tgtaacatca aagcccacgt aaaggttgct tccactgaaa acggaatcat ctttggaaac   2400
atcgtttatg acgtgacggg cgcggcctca gacaggaacg tagtcgtcct caatgacatc   2460
cacatcgaca tcatggacta tattgttcca gcgtcttgta ccgattcaga atttatgagg   2520
atgtgggctg aattcgaatg ggaaaataag gtgactgtca acacacctct gacggacctt   2580
gccgactact tggagcacct cattaagagc accaacatga aatgcttgac gccagaaaag   2640
gcgctcagcg gtcagtgtgg tttcatggca gccaatatgt acgctaaatc catatttgga   2700
gaagacgctt tggccaattt gagtatagag aaaccgttta acaaaccaga agcacctgta   2760
gctggacaca tcagaatcag ggctaagagt cagggcatgg ccttgagctt aggagacaaa   2820
ataaatatga ctcaaaaagg cataccaagt aagattgttg catcttga                 2868
```

<210> SEQ ID NO 10
<211> LENGTH: 1098
<212> TYPE: DNA
<213> ORGANISM: Diabrotica virgifera

<400> SEQUENCE: 10

```
cctgtacttt cctgtatcct catgttcact gtctaccgtt ttactcactt cctttgttaa     60
tactaatacc atttcttcta tgttccgtga agagactaat tcaagggcta gacttaaagt    120
```

```
cttcttgcgg acttctaagt caggagcaga gagtactctc agtatgtcca taactaaatc    180

ctgcagaatt ctttcgtgat taggaagctc cttaagtgct atcagcctgt ccaaaacgat    240

gagttttaca ttgttgtcac tttctttgat aattaactca atgtaacagc tagcagcagc    300

tttaacggca gtcggggcac tggagagggt gactaaagtt cctgcagctt cgtacctgac    360

agcaggactg cttgagttca acaagttata tatacatcta ataaatctag atctttccgc    420

aggattggaa tgacacacct tatatatcaa ctcaacgatg accagttgta gaatatctcc    480

aaatgaattt acttgatcta aacatgatgc caaatacgac aacgcccttt cttggtcagc    540

atgaagaagc attaaaaacg catttctttt acaagacatg tcttgctcac catccaaata    600

attggagatc agttcaggag catctggaat gagggcttca aaatttttgt aaatggtaaa    660

aattgccagt acagcattcc tcctcacata gctgtgccta tgatccaaac aagctctaat    720

actgggcatt aatggttcca acaattctgg ttccttcagt ttgcacaaga agcgaagtgt    780

agaacctctc aaaaattcat ttgggtgttg cagatctttt ctataggcat cacataccaa    840

aatcatctct tgtagtagtt taccttctgg atttgttttt ggaactattt cccagaaaat    900

caataatagt ttttttgcca aatgatcttg tagaggtaaa acgtttctta taatggtcat    960

taggaatcca ttcggcaacc tttctcctgc cagaatcatg tgaattattt tttctaatgc   1020

tcttattttt actttaacct caccctttc taaatccatt tttagttgca tttcattgta   1080

gggctccgaa tctgttgg                                                  1098
```

<210> SEQ ID NO 11
<211> LENGTH: 720
<212> TYPE: DNA
<213> ORGANISM: Meligethes aeneus

<400> SEQUENCE: 11

```
gtaacacaat tgaccggttt ttcggatcca gtttacgcag aagcatacgt acacgtaaac     60

caatacgata tagttctgga tgtacttatt gttaaccaaa caaacgatac cctacaaaat    120

tgcaccctag aattagcaac actgggcgac ttaaaacttg tggaaaaacc tcaacccgta    180

gtacttgcac ctcgcgactt ctgcaatatt aaagctaacg taaaagtggc ctcaaccgaa    240

aatggtatta tattcggtaa tatcgtttac gatgtgaccg gtgccgcttc agatcgcaat    300

gttgttgttc tcaacgacat tcatatcgat attatggact acattgtacc agcttcttgc    360

aacgattctg aattcatgag gatgtgggcg gaattcgaat gggaaaacaa agtaaccgtt    420

aacaccccca ttacggacct tgcggaatac cttaaacatc tcattaaaag taccaatatg    480

aaatgcttga ctccggaaaa ggctttgtcc ggtcagtgtg gatttatggc ggccaacatg    540

tatgctaaat ctatttttgg agaggatgct ttggctaatt taagtattga gaagcctttt    600

aataagcctg atgccccagt ggctggacat attcgtataa gagctaagag tcagggaatg    660

gctttaagtc ttggagataa gatcaatatg acccaaaaag gtctgcacaa cagcaaagta    720
```

<210> SEQ ID NO 12
<211> LENGTH: 761
<212> TYPE: DNA
<213> ORGANISM: Sitophilus oryzae

<400> SEQUENCE: 12

```
accttgcatt cttgctgtat aaagtttcct gatgttgctg ccacagttat accgattttg     60

gtagagtttt tgtcagataa taacgagcta gctgccgcag atgtgttagt tttgtaaga     120
```

```
gaggccatac aaaagttcga ggcacttaga ccacttatta ttgagaaact tcttgaagct    180

ttcaaggata taaaatcagt gaaagtccat agggctgccc tgtggattct tggagagtat    240

gctacatcgg ttgctgatat agagtcagtc ataaaagagg tgacatatac attgggcgag    300

ggttcttttg ttgtagccga acacagactc aatcaaggcg aagtagacga aaaagaaata    360

gaaaacatag gaaacggtcc tgtcgtgact actctagtga cgtcagacgg tacctacgcc    420

actcagtcgg cgtttaacac tgttcagaaa tcgaaaaaag aaagaccgcc tttaaggcag    480

taccttatgg acggagattt cttcattgga gcttctctgg cttcaacttt gaccaaactg    540

gctttgagat ttggtcagct ggtttctgca gaaagaacca acagatttga cgcagaggtc    600

atgttgatta tggcggggat actgcatttg ggccaatcag gcttgccaac caaatcgatc    660

acaaacgacg acagggacca tatcttgctc tgcctgaagg tagtctctga cagatcgcct    720

gtcatagttc agatctttac cgactattgt aggaaggccc t                        761
```

```
<210> SEQ ID NO 13
<211> LENGTH: 668
<212> TYPE: DNA
<213> ORGANISM: Sitophilus granarius

<400> SEQUENCE: 13

gaaaggcctt aaacgacatg ctattggcca aagagcgcga ggaagcgtcc aatcagaagg     60

ccaaagaaaa aacagggcac aaaattcaaa cggacgatcc gatcaatttc attcagctgg    120

agactgataa gggtggagaa ttgggcgaga acgtattcga aacgtcgtta tcgcaagcgc    180

tgattggggg aagagccgcg ggcggggaca ctggtttagg tccaaataaa ctggacaaag    240

tcactcaact cacaggtttc tcggatccgg tatattcaga ggcgtacgtg cacgtgaatc    300

agtacgacat cgttttggac gtactgatcg tgaatcagac caacgacacg ttgcagaact    360

gtacgttaga gctggcaacg ttgggcgacc tgaaattggt ggaaaaacct caacccgttg    420

ttttggcccc taaagatttc tgcaatatta aagcaaacgt taaggttgct tccactgaaa    480

atggtattat attcggcaac attgtctatg acgtcaccgg cgccgcgtct gacagaaatg    540

tcgtcgtttt gaacgacata cacatagaca ttatggacta cattgtgcca gccagttgca    600

ccgacacaga gtttatgcgc atgtgggcgg aatttgagtg ggagaacaag gtaactgtca    660

acacatcc                                                             668
```

```
<210> SEQ ID NO 14
<211> LENGTH: 755
<212> TYPE: DNA
<213> ORGANISM: Ceuthorrhynchus assimilis

<400> SEQUENCE: 14

cctgacgctc cagaacttat ttcaaattac ttagatagcg aacaagatat gtcgtgcaaa     60

aggaacgcct ttttaatgtt gctacatgct gatcaagaca gagctttatc ttatttgagc    120

tcttgcttag atcaagttac ttcttttgga gatattttac aactggttat tgtagaactg    180

atttataagg tttgtcatac caacccatca gaaagatcca gattcatccg ttgcatatac    240

aatttgctaa actctagtag tgccgcagta agatatgaag ctgcaggcac tcttattaca    300

ttatccagtg cccctactgc tatcagagcg gcggcttctt gttacattga tttaattgtc    360

aaggagagcg acaataatgt taaactaatt gttttggata agttggttgc ccttggcgaa    420

catccaacct ataacagggt tttgcaggat ctcgttatgg atatactaag agttttgagt    480

agtcctgatt tagaagtgag aaggaaaact ttaaatttag ccatggaact agtgaattct    540
```

```
agaaatattg aggaaactgt tttgtttttg aaaaaagaag tttcaaaaac tttagattct    600

gaacatgaag atacaggcaa atataggcaa cttcttgtaa gaactttgca ttcctgctgt    660

attaaatttc ctgatgttgc tgccacagtg attccagttt tggtggaatt tttgtctgat    720

accaatgagt tagctgctgc tgatgttttg gtgtt                               755
```

<210> SEQ ID NO 15
<211> LENGTH: 662
<212> TYPE: DNA
<213> ORGANISM: Rhyzoperta dominica

<400> SEQUENCE: 15

```
tgaaacctca ctctcacaag cacttgctgg tggccgtcct ggtacagctg acctagcagc     60

ttccatcagc aaattaaaca aagtaacaca attaactggc ttctcagatc cagtgtatgc    120

tgaagcttat gtacatgtaa atcagtatga tattgtgctg gatgttttga ttgtgaatca    180

gactaatgat actttacaaa actgcacctt ggaactggcg acattaggtg atctaaaact    240

tgttgagaaa ccgcagcctg ttgtgcttgc acctaaagat ttctgtaata taaaggcaaa    300

tgttaaggtt gcatctacag aaaatggtat catttttgga aacattgtgt atgatattac    360

tggtgctgcc tcagatagaa atgttgttgt tttgaatgac atacacattg acattatgga    420

ttacattgtt cctgcatctt gtaatgatac tgaatttaga cagatgtggg cagagtttga    480

atgggaaaat aaggtttctg tgagcaccac attgacagat ttagcagaat atctcaaact    540

cttgattaag agtacaaata tgaagtgctt aaccccagag aaggcccttt ctggacagtg    600

tggatttatg gcagccaata tgtatgccaa gtctatattt ggtgaagatg ccttggctaa    660

tt                                                                   662
```

<210> SEQ ID NO 16
<211> LENGTH: 769
<212> TYPE: DNA
<213> ORGANISM: Phyllotreta nemorum

<400> SEQUENCE: 16

```
ggagccttac aatgaaatgc aattgaaaat ggacctcgaa aagggcgaag tcaaagtaaa     60

gataagggct ttggaaagaa tcatacacat gatattggca ggcgagagat tgcccaacgg    120

attcctgatg acaatcatac gaaacgtttt gcccctacaa gatcacctgg ccaagaaact    180

tttgctcatt ttttgggaaa tcgtgccgaa aaccaccccc gacggtaaat tactgcagga    240

aatgatccta gtctgtgacg cctacagaaa ggacctgcag caccccaacg aatttttgag    300

gggctccaca ttgagattcc tatgcaagct gaaggagccc gagctgttgg agcctctgat    360

gcccagcatt cgaatttgcc tcgaacacag gcacagctac gttcgaagga atgccgttct    420

ggccattttt acgatataca agaatttcga attcctcatt ccagacgccc ctgaattgat    480

ttctacttat ctagacggcg agcaagatat gtcttgtaaa agaaacgctt tccttatgct    540

tttgcatgcc gaccaagatc gagccctcac ttacctatcc aattgcttag atcaagtggc    600

ttcttttggg gatattctac agttggttat tgttgaattg atatacaaag tgtgccactc    660

caaccccgcc gagagatcca gattcattcg atgcatatac aatctattaa attcgagcag    720

tcctgctgtt cggtacgagg ccgccggtac tctgattact ctgtccagc                769
```

<210> SEQ ID NO 17
<211> LENGTH: 787
<212> TYPE: DNA

<213> ORGANISM: Psylliodes chrysocephala

<400> SEQUENCE: 17
tgtcagatat gaagctgctg gtacacttgt aacactttca agtgctccca cagcagtaaa 60
agcagctgct agttgttata ttgaactaat tatcaaggaa agtgataata atgtaaagtt 120
gattgtcttg gacagattga ttgcccttaa ggaacatccc agccatgaaa gggttttgca 180
agatttggtt atggatatat taagagtgtt gcaagctcct gacttggaag ttcgcaaaaa 240
gactttaaac ctagcacttg aactggtatc atctcgtaat atagaagaaa tggttttggt 300
tcttaaaaag gaggtatcaa aaaccgtaga tagcgagcac gaagatacag gaaaatacag 360
gcagttactt gttagaacac ttcattcttg ttgtataaaa ttcccagatg tagctgtaac 420
tgtcattcct gttttaatgg aatttttgtc tgatagtaac gagttagctg ctactgacgt 480
gttactattt ttgagagagg ccatacagaa gtttgataat ctgcaaccac ttattattga 540
gaaacttcta gaaacattca aagatataaa atctgttaaa gtgcatagag cagctctttg 600
gatattggga gaatatgcca cttctgtctc agacattgaa gctgttatta aagaaattaa 660
tcaaacctta ggagaagctc ctctgttgga aactgaacaa aaactaattt ctggagagac 720
agacgacaca actacagttc caacaggtgg agctacaact ttggttactt cagatggtac 780
ttacgcc 787

<210> SEQ ID NO 18
<211> LENGTH: 747
<212> TYPE: DNA
<213> ORGANISM: Phyllotreta striolata

<400> SEQUENCE: 18
acttacctag atggcgaaca agacatgtct tgtaaaagga acgcttttct tatgctcttg 60
cacgccgatc aagatcgagc cctcacttat ctatccaatt gtttagatca agtcgcttcc 120
ttcggggata tccttcagtt ggttatcgtc gaattgatat acaaggtgtg ccactctaac 180
cccaccgaga gatccagatt cattcgatgc atatacaatc tgttaaattc gagcagtcct 240
gctgttagat acgaagcggc aggtactctc attactttgt ccagcgctcc gactgctata 300
aaagccgccg ccagttgtta catcgaattg atcattaaag agagcgacaa caacgtcaaa 360
ttgatcgttt tggatagatt gatcgcgttg aaggaacatc cgagccacga gagagtccta 420
caggacttgg ttatggatat attgagagtg ttatcggctc ccgatttgga ggtgcgaaag 480
aaaacgctta atttagcgct cgaattggtg tcctctcgta acgtcgaaga aatggtgttt 540
gtgctgaaga aggaggtgtc gaagaccatg gatagcgaac acgaagatac cgggaaatac 600
aggcaactgt tggtcagaac gttgcattct tgttgcatca aattccccga tatagctgct 660
acggtcattc ccgttctaat ggagttcctg tccgatagca acgaattggc ggccaccgat 720
gtgttgctat ttctgaggga agccata 747

<210> SEQ ID NO 19
<211> LENGTH: 742
<212> TYPE: DNA
<213> ORGANISM: Leptinotarsa decemlineata

<400> SEQUENCE: 19
gttgatcatg gcaggaattg ttcatttggg aaaatcaggc ttgccaacga aaccgatcac 60
gaatgacgat aaggatcaca tcctgttctg tctgagggtt ctctccgatc gtacttccgc 120
catcattcag atattcacag agcgctgccg gctcgctctc aatgacatgc ttgtcgccaa 180

```
agaagcagaa gaggcgtcga ctctgaagac gaaagagaaa tccggcaata cgatccaaac    240

agatgacccg attagcttcc tccagctaga ggccgacaag aatggagaac ttggcgaaaa    300

cgtatttgag acctcgctgt cgcaagccct cgtcggtgga agaggcagcg cggcagattc    360

tgccacagga acaaataagt tgaacaagat aacgcagttg acaggttttt cggatcccgt    420

ttattcagaa gcttatgtcc acgtcaacca gtacgatatt gtgctggacg ttttgatcgt    480

caatcaaact aatgatactc tgcaaaattg tactttggag ctggcgacgt tgggagatct    540

gaaacttgtc gaaaaacctc agccagtagt tcttgctccc aaagacttct gtaacatcaa    600

agcccacgta aaggttgctt ccactgaaaa cggaatcatc tttggaaaca tcgtttatga    660

cgtgacgggc gcggcctcag acaggaacgt agtcgtcctc aatgacatcc acatcgacat    720

catggactat attgttccag cg                                             742
```

```
<210> SEQ ID NO 20
<211> LENGTH: 720
<212> TYPE: RNA
<213> ORGANISM: Meligethes aeneus

<400> SEQUENCE: 20

guaacacaau ugaccgguuu uucggaucca guuuacgcag aagcauacgu acacguaaac     60

caauacgaua uaguucugga uguacuuauu guuaaccaaa caaacgauac ccuacaaaau    120

ugcacccuag aauuagcaac acugggcgac uuaaaacuug uggaaaaacc ucaacccgua    180

guacuugcac cucgcgacuu cugcaauauu aaagcuaacg uaaaagugge cucaaccgaa    240

aaugguauua uauucgguaa uaucguuuac gaugugaccg gugccgcuuc agaucgcaau    300

guuguuguuc ucaacgacau ucauaucgau auuauggacu acauuguacc agcuucuugc    360

aacgauucug aauucaugag gaugugggcg gaauucgaau gggaaaacaa aguaaccguu    420

aacaccccca uuacggaccu ugcggaauac cuuaaacauc ucauuaaaag uaccaauaug    480

aaaugcuuga cuccggaaaa ggcuuugucc ggucagugug gauuuauggc ggccaacaug    540

uaugcuaaau cuauuuuugg agaggaugcu uuggcuaauu uaaguauuga gaagccuuuu    600

aauaagccug augccccagu ggcuggacau auucguauaa gagcuaagag ucagggaaug    660

gcuuuaaguc uuggagauaa gaucaauaug acccaaaaag gucugcacaa cagcaaagua    720
```

```
<210> SEQ ID NO 21
<211> LENGTH: 761
<212> TYPE: RNA
<213> ORGANISM: Sitophilus oryzae

<400> SEQUENCE: 21

accuugcauu cuugcuguau aaaguuuccu gauguugcug ccacaguuau accgauuuug     60

guagaguuuu ugucagauaa uaacgagcua gcugccgcag auguguuagu uuuuguaaga    120

gaggccauac aaaaguucga ggcacuuaga ccacuuauua uugagaaacu ucuugaagcu    180

uucaaggaua uaaaaucagu gaaaguccau agggcugccc uguggauucu uggagaguau    240

gcuacaucgg uugcugauau agagucaguc auaaaaagagg ugacauauac auugggcgag    300

gguucuuuug uuguagccga acacagacuc aaucaaggcg aaguagacga aaaagaaaua    360

gaaaacauag gaaacggucc ugucgugacu acucuaguga cgucagacgg uaccuacgcc    420

acucagucgg cguuuaacac uguucagaaa ucgaaaaaag aaagaccgcc uuuaaggcag    480

uaccuuaugg acggagauuu cuucauugga gcuucucugg cuucaacuuu gaccaaacug    540
```

```
gcuuugagau uuggucagcu gguuucugca gaaagaacca acagauuuga cgcagagguc    600

auguugauua uggcggggau acugcauuug ggccaaucag gcuugccaac caaaucgauc    660

acaaacgacg acagggacca uaucuugcuc ugccugaagg uagucucuga cagaucgccu    720

gucauaguuc agaucuuuac cgacuauugu aggaaggccc u                        761


<210> SEQ ID NO 22
<211> LENGTH: 668
<212> TYPE: RNA
<213> ORGANISM: Sitophilus granarius

<400> SEQUENCE: 22

gaaaggccuu aaacgacaug cuauuggcca aagagcgcga ggaagcgucc aaucagaagg     60

ccaaagaaaa aacagggcac aaaauucaaa cggacgaucc gaucaauuuc auucagcugg    120

agacugauaa ggguggagaa uugggcgaga acguauucga aacgucguua ucgcaagcgc    180

ugauuggggg aagagccgcg ggcggggaca cugguuuagg uccaaauaaa cuggacaaag    240

ucacucaacu cacagguuuc ucggauccgg uauauucaga ggcguacgug cacgugaauc    300

aguacgacau cguuuuggac guacugaucg ugaaucagac caacgacacg uugcagaacu    360

guacguuaga gcuggcaacg uugggcgacc ugaaauuggu ggaaaaaccu caacccguug    420

uuuuggcccc uaaagauuuc ugcaauauua aagcaaacgu uaagguugcu uccacugaaa    480

augguauuau auucggcaac auugucuaug acgucaccgg cgccgcgucu gacagaaaug    540

ucgucguuuu gaacgacaua cacauagaca uuauggacua cauugugcca gccaguugca    600

ccgacacaga guuuaugcgc augugggcgg aauuugagug ggagaacaag guaacuguca    660

acacaucc                                                             668


<210> SEQ ID NO 23
<211> LENGTH: 755
<212> TYPE: RNA
<213> ORGANISM: Ceuthorrhynchus assimilis

<400> SEQUENCE: 23

ccugacgcuc cagaacuuau uucaaauuac uuagauagcg aacaagauau gucgugcaaa     60

aggaacgccu uuuuaauguu gcuacaugcu gaucaagaca gagcuuuauc uuauuugagc    120

ucuugcuuag aucaaguuac uucuuuugga gauauuuuac aacugguuau uguagaacug    180

auuuauaagg uuugucauac caacccauca gaaagaucca gauucauccg uugcauauac    240

aauuugcuaa acucuaguag ugccgcagua agauaugaag cugcaggcac ucuuauuaca    300

uuauccagug ccccuacugc uaucagagcg gcggcuucuu guuacauuga uuuaauuguc    360

aaggagagcg acaauaaugu uaaacuaauu guuuuggaua aguugguugc ccuuggcgaa    420

cauccaaccu auaacagggu uuugcaggau cucguuaugg auauacuaag aguuuugagu    480

aguccugauu uagaagugag aaggaaaacu uuaaauuuag ccauggaacu agugaauucu    540

agaaauauug aggaaacugu uuuguuuuug aaaaaagaag uuucaaaaac uuuagauucu    600

gaacaugaag auacaggcaa auauaggcaa cuucuuguaa gaacuuugca uuccugcugu    660

auuaaauuuc cugauguugc ugccacagug auuccaguuu ugguggaauu uuugucugau    720

accaaugagu uagcugcugc ugauguuuug guguu                               755


<210> SEQ ID NO 24
<211> LENGTH: 662
<212> TYPE: RNA
<213> ORGANISM: Rhyzoperta dominica
```

<400> SEQUENCE: 24

```
ugaaaccuca cucucacaag cacuugcugg uggccguccu gguacagcug accuagcagc     60

uuccaucagc aaauuaaaca aaguaacaca auuaacuggc uucucagauc caguguaugc    120

ugaagcuuau guacauguaa aucaguauga uauugugcug gauguuuuga uugugaauca    180

gacuaaugau acuuuacaaa acugcaccuu ggaacuggcg acauuaggug aucuaaaacu    240

uguugagaaa ccgcagccug uugugcuugc accuaaagau uucuguaaua uaaaggcaaa    300

uguuaagguu gcaucuacag aaaaugguau cauuuuugga aacauugugu augauauuac    360

uggugcugcc ucagauagaa auguuguugu uuugaaugac auacacauug acauuaugga    420

uuacauuguu ccugcaucuu guaaugauac ugaauuuaga cagauguggg cagaguuuga    480

augggaaaau aagguuucug ugagcaccac auugacagau uuagcagaau aucucaaacu    540

cuugauuaag aguacaaaua ugaagugcuu aaccccagag aaggcccuuu cuggacagug    600

uggauuuaug gcagccaaua uguaugccaa gucuauauuu ggugaagaug ccuuggcuaa    660

uu                                                                   662
```

<210> SEQ ID NO 25
<211> LENGTH: 769
<212> TYPE: RNA
<213> ORGANISM: Phyllotreta nemorum

<400> SEQUENCE: 25

```
ggagccuuac aaugaaaugc aauugaaaau ggaccucgaa aagggcgaag ucaaaguaaa     60

gauaagggcu uuggaaagaa ucauacacau gauauuggca ggcgagagau ugcccaacgg    120

auuccugaug acaaucauac gaaacguuuu gccccuacaa gaucaccugg ccaagaaacu    180

uuugcucauu uuuugggaaa ucgugccgaa aaccaccccc gacgguaaau uacugcagga    240

aaugauccua gucugugacg ccuacagaaa ggaccugcag caccccaacg aauuuuugag    300

gggcuccaca uugagauucc uaugcaagcu gaaggagccc gagcuguugg agccucugau    360

gcccagcauu cgaauuugcc ucgaacacag gcacagcuac guucgaagga augccguucu    420

ggccauuuuu acgauauaca agaauuucga auuccucauu ccagacgccc cugaauugau    480

uucuacuuau cuagacggcg agcaagauau gucuuguaaa agaaacgcuu uccuuaugcu    540

uuugcaugcc gaccaagauc gagcccucac uuaccuaucc aauugcuuag aucaaguggc    600

uucuuuuggg gauauucuac aguugguuau uguugaauug auauacaaag ugugccacuc    660

caaccccgcc gagagaucca gauucauucg augcauauac aaucuauuaa auucgagcag    720

uccugcuguu cgguacgagg ccgccgguac ucugauuacu cuguccagc               769
```

<210> SEQ ID NO 26
<211> LENGTH: 787
<212> TYPE: RNA
<213> ORGANISM: Psylliodes chrysocephala

<400> SEQUENCE: 26

```
ugucagauau gaagcugcug guacacuugu aacacuuuca agugcuccca cagcaguaaa     60

agcagcugcu aguuguuaua uugaacuaau uaucaaggaa agugauaaua auguaaaguu    120

gauugucuug gacagauuga uugcccuuaa ggaacauccc agccaugaaa ggguuuugca    180

agauuugguu auggauauau uaagaguguu gcaagcuccu gacuuggaag uucgcaaaaa    240

gacuuuaaac cuagcacuug aacugguauc aucucguaau auagaagaaa ugguuuuggu    300
```

```
ucuuaaaaag gagguaucaa aaaccguaga uagcgagcac gaagauacag gaaaauacag    360

gcaguuacuu guuagaacac uucauucuug uuguauaaaa uucccagaug uagcuguaac    420

ugucauuccu guuuuaaugg aauuuuuguc ugauaguaac gaguuagcug cuacugacgu    480

guuacuauuu uugagagagg ccauacagaa guuugauaau cugcaaccac uuauuauuga    540

gaaacuucua gaaacauuca aagauauaaa aucuguuaaa gugcauagag cagcucuuug    600

gauauuggga gaauaugcca cuucugucuc agacauugaa gcuguuauua aagaaauuaa    660

ucaaaccuua ggagaagcuc cucuguugga aacugaacaa aaacuaauuu cuggagagac    720

agacgacaca acuacaguuc caacaggugg agcuacaacu uugguuacuu cagaugguac    780

uuacgcc                                                               787
```

<210> SEQ ID NO 27
<211> LENGTH: 747
<212> TYPE: RNA
<213> ORGANISM: Phyllotreta striolata

<400> SEQUENCE: 27

```
acuuaccuag auggcgaaca agacaugucu uguaaaagga acgcuuuucu uaugcucuug     60

cacgccgauc aagaucgagc ccucacuuau cuauccaauu guuuagauca agucgcuucc    120

uucggggaua uccuucaguu gguuaucguc gaauugauau acaaggugug ccacucuaac    180

cccaccgaga gauccagauu cauucgaugc auauacaauc uguuaaauuc gagcaguccu    240

gcuguuagau acgaagcggc agguacucuc auuacuuugu ccagcgcucc gacugcuaua    300

aaagccgccg ccaguuguua caucgaauug aucauuaaag agagcgacaa caacgucaaa    360

uugaucguuu uggauagauu gaucgcguug aaggaacauc cgagccacga gagaguccua    420

caggacuugg uuauggauau auugagagug uuaucggcuc ccgauuugga ggugcgaaag    480

aaaacgcuua auuuagcgcu cgaauuggug uccucucgua acgucgaaga aaugguguuu    540

gugcugaaga aggaggugucc gaagaccaug gauagcgaac acgaagauac cgggaaauac    600

aggcaacugu uggucagaac guugcauucu uguugcauca aauuccccga uauagcugcu    660

acggucauuc ccguucuaau ggaguuccug uccgauagca acgaauuggc ggccaccgau    720

guguugcuau uucugaggga agccaua                                         747
```

<210> SEQ ID NO 28
<211> LENGTH: 742
<212> TYPE: RNA
<213> ORGANISM: Leptinotarsa decemlineata

<400> SEQUENCE: 28

```
guugaucaug gcaggaauug uucauuuggg aaaaucaggc uugccaacga aaccgaucac     60

gaaugacgau aaggaucaca uccuguucug ucugaggguu cucuccgauc guacuuccgc    120

caucauucag auauucacag agcgcugccg gcucgcucuc aaugacaugc uugucgccaa    180

agaagcagaa gaggcgucga cucugaagac gaaagagaaa uccggcaaua cgauccaaac    240

agaugacccg auuagcuucc uccagcuaga ggccgacaag aauggagaac uuggcgaaaa    300

cguauuugag accucgcugu cgcaagcccu cgucggugga agaggcagcg cggcagauuc    360

ugccacagga acaaauaagu ugaacaagau aacgcaguug acagguuuuu cggaucccgu    420

uuauucagaa gcuuaugucc acgucaacca guacgauauu gugcuggacg uuuugaucgu    480

caaucaaacu aaugauacuc ugcaaaauug uacuuuggag cuggcgacgu ugggagaucu    540

gaaacuuguc gaaaaaccuc agccaguagu ucuugcuccc aaagacuucu guaacaucaa    600
```

```
agcccacgua aagguugcuu ccacugaaaa cggaaucauc uuuggaaaca ucguuuauga    660

cgugacgggc gcggccucag acaggaacgu agucguccuc aaugacaucc acaucgacau    720

cauggacuau auuguuccag cg                                             742
```

<210> SEQ ID NO 29
<211> LENGTH: 2883
<212> TYPE: RNA
<213> ORGANISM: Meligethes aeneu

<400> SEQUENCE: 29

```
augacugcug uagaacagcc cuguuacacu uuaauuaauu uacccaccga uucggagccu     60

uacaaugaaa ugcagcuuaa gcaggauuua gaaaaaggag aaauuaagca aaagguugaa    120

gcccucaaga aaauuauaca caugauuuug gcaggugaaa gauuaccccc aggcuuuuua    180

auguuaauaa uaagguaugu uuuaccacug caagaccauu uagccaaaaa guuguuacuu    240

auauuuuggg aaauuguucc caaaacuaca caagauggaa aauuauuaca agaaaugaua    300

uugguuugug augcuuaccg uaaggauuua caacauccca augaauuuuu acgcgguucu    360

acauuaagau uuuuguguaa auuaaaagaa ccugagcuuu uggaaccccu aaugccaucc    420

auacguucuu gcuuggagca uagacacucu uauguacgua gaaaugcugu acuugcuauu    480

uucacuauuu acagaaacuu ugaauucuua auuccugaug caccugaguu aaauaucaacu    540

uacuuggaag gugaacauga uaugucuugu aaacguaaug cuuuccuaau guuguuacau    600

gcugaucagg auagagcucu aucguacuug gcuaauuguu uggaucaagu aaauacuuuu    660

ggggauauuu ugcaguuggu uauaguggag uugauuuaua agguuugcca uucaaauccu    720

gcagaaagau caagauuuau uaggguguauu uauaauuugu ugaauucaag uagcccugcu    780

guaagauaug aggcugcagg uacuuugguu accuugucaa augcucccac ugcaauuaaa    840

gcugcugcga guuguuacau ugaauugauu auuaaggaaa gugauaauaa uguuaaacua    900

auuguuuugg aucgauugau ugcucuaaaa gaacauccaa gucaugaaag aguucuacaa    960

gaucuaguga uggacauucu gagaguucua ucaagcccug acuuggaggu uagaaaaaaa   1020

acguuaaauu uagcuuugga uuugguuucg ucaagaaaua uugaagaaau gguuuugguu   1080

uugaaaaaag aaguuuccaa aacucaugau guagagcaug aggauacagg aaaguaccga   1140

caacuuuugg ucaggacuuu acauacaugc uccauuaagu uuccugauau ugcugccacu   1200

guaauaccag uauuggugga auucuugucu gacacaaaug aguuagcugc cacugauguu   1260

uuggguguuug uaagagaggc uauacagaag uuugauaauc uacaaccacu uauuauugag   1320

aaacuuuugg aaugcuuccg cgacauaaaa uccguaaaag uucacagggc ggccuugugg   1380

auuuugggag aguaugcuac ugaagugaac gauauugagu ccguucuuaa agaaauuaau   1440

ucggcucuug gugaaggucc ucuucuggag gcagaacaac gguuggugguc uggugauucc   1500

gaugagggau cgaagccggc uauggcucaa aauaccgcac caucagccuc ccuuguuacc   1560

ucugauggua cuuaugcaac acaaucugcu uucaacacag ugcaaaaaga uaaagaaguu   1620

aagaggccac cacuaagaca guaccuaaug gacggugauu ucuuuauugg agcugcuuug   1680

gccucaaccc uaaccaaacu ggcucuaaga uaugcaaaau ugaaugagca ucuaaaagca   1740

aacagguuug augccgaaau uauguuaauu auggcaggaa uuauacauuu gggaaaguca   1800

ggcuugccua caaaaccaau caccaacgac gacaaagacc auauucuauu uugucuucgc   1860

guuauaucgg accguagucc caccaucauc gaaguauucg ugcaauugug ucguaacgcg   1920
```

cuaaacgaua ugcucaucgc uaaagagauu gaagaagccu cgacucaaaa agcuaaagaa 1980
aaagccggua acuugaucca aaccgaugau ccaauuaauu ucaugcaauu agaaagugau 2040
agaucagggg aauugggcga aaacguuuuc gagaugucgu ugaaucaggc cguaauaggc 2100
ggccgugguc agggucaaga uucuaauaca gggguaaaua aguuaaauaa gguaacacaa 2160
uugaccgguu uuucggaucc aguuuacgca gaagcauacg uacacguaaa ccaauacgau 2220
auaguucugg auguacuuau uguuaaccaa acaaacgaua cccuacaaaa uugcacccua 2280
gaauuagcaa cacugggcga cuuaaaacuu guggaaaaac cucaacccgu aguacuugca 2340
ccucgcgacu ucugcaauau uaaagcuaac guaaaagugg ccucaaccga aaaugguauu 2400
auauucggua auaucguuua cgaugugacc ggugccgcuu cagaucgcaa uguuguuguu 2460
cucaacgaca uucauaucga uauuauggac uacauuguac cagcuucuug caacgauucu 2520
gaauucauga ggauguggc ggaauucgaa ugggaaaaca aaguaaccgu uaacaccccc 2580
auuacggacc uugcggaaua ccuuaaacau cucauuaaaa guaccaauau gaaaugcuug 2640
acuccggaaa aggcuuuguc cggucagugu ggauuuaugg cggccaacau guaugcuaaa 2700
ucuauuuuug gagaggaugc uuuggcuaau uuaaguauug agaagccuuu uaauaagccu 2760
gaugccccag uggcuggaca uauucguaua agagcuaaga gucagggaau ggcuuuaagu 2820
cuuggagaua agaucaauau gacccaaaaa ggucugcaca acagcaaagu aaccgcgggu 2880
uaa 2883

<210> SEQ ID NO 30
<211> LENGTH: 2877
<212> TYPE: RNA
<213> ORGANISM: Sitophilus oryzae

<400> SEQUENCE: 30
augacgagcg ucgaacagcc cuguuacacc cugaucaaug ugucuucgga uacagagccc 60
uacaacgaga ugcauuugaa aagcgaucuc gagaagggcg auacagacca aaaggucgaa 120
gcauuaaaga agauuauucg aaugaucuug gcaggcgaaa gauuaccucc agguuuccuc 180
augaugauua uucgcuacgu ucuuccuuug caagaccaca cagcuaaaaa acuccuacuu 240
auauucuggg aaauuguccc uaaaacuaca cccgauggca agcuucugca agaaaugauu 300
cuaguuugug acgcuuacag aaaagacuua caacacccua acgaguucuu acgcgguucc 360
accuugagau uucucugcaa acugaaggaa ccagagcuuc ucgaaccuuu aaugccuuca 420
auaagggcuu guuuagaaca cagacauagc uacguuagga gaaacgcagu gcuugcuauu 480
uuuacaauau acaggaacuu ugaguuucuu auacccgaug cuccagaacu gauaucaacu 540
uauuuagaug gagaacagga uaugucuugu aaaagaaaug cguuuuugau guugcugcau 600
gccgaucagg auagggcacu gucuuauuug aguucuuguc ucgaucaagu cacuucuuuu 660
ggagauauuc uucaguuagu uauaguggag uugauauaca aggugugcca uucaaauccc 720
acagaaagau caagauuuau cagguguauu uauaauuuac uuaacucaag uagugcggcu 780
guuagguaug aagcugcagg uacucuuaua acucuaucca gugcaccuac agcuauuaaa 840
gcugcugcuu cauguuauau ugaucuuauc aucaaggaaa gcgauaauaa uguuaaacuu 900
auuguccugg acaaacuagu aacucuaggg gaacauccaa acuauaacag aguucuucag 960
gacuugguaa uggauauuuu aagaguuuua ucuaguccgg accuggaagu aagaagaaaa 1020
accuuaaauc uagccaugga gcugguuaau uccaggaaua uugaagaaau ggucuuguuc 1080
uugaagaaag aaguaucaaa aacccuugac ucugagcaug aagauacagg aaaauaccga 1140

```
caacucuugg ucaggaccuu gcauucuugc uguauaaagu uuccugaugu ugcugccaca   1200

guuauaccga uuuugguaga guuuuuguca gauaauaacg agcuagcugc cgcagaugug   1260

uuaguuuuug uaagagaggc cauacaaaag uucgaggcac uuagaccacu uauuauugag   1320

aaacuucuug aagcuuucaa ggauauaaaa ucagugaaag uccauagggc ugcccugugg   1380

auucuuggag aguaugcuac aucgguugcu gauauagagu cagucauaaa agaggugaca   1440

uauacauugg gcgaggguuc uuuuguugua gccgaacaca gacucaauca aggcgaagua   1500

gacgaaaaag aaauagaaaa cauaggaaac gguccugucg ugacuacucu agugacguca   1560

gacgguaccu acgccacuca gucggcguuu aacacuguuc agaaaucgaa aaaagaaaga   1620

ccgccuuuaa ggcaguaccu uauggacgga gauuucuuca uuggagcuuc ucuggcuuca   1680

acuuugacca aacuggcuuu gagauuuggu cagcugguuu cugcagaaag aaccaacaga   1740

uuugacgcag aggucauguu gauuauggcg gggauacugc auuugggcca aucaggcuug   1800

ccaaccaaau cgaucacaaa cgacgacagg gaccauaucu ugcucugccu gaagguaguc   1860

ucugacagau cgccugucau aguucagauc uuuaccgacu auuguaggaa ggcccugaac   1920

gacaugcuau uggccaaaga gcgcgaggaa gcgucaaauc agaaggccaa agaaaaaaca   1980

gggcacaaaa uucaaacgga cgacccgauc aauuucauuc aguuggagac ugauaagggu   2040

ggcgaauugg gggaaaaugu auucgaaacg ucguuaucuc aagcucugau uggaggaaga   2100

gccgcaggcg gggacacugg uuugggucca aauaaacugg acaaagucac ccaacucaca   2160

gguuucucag auccgguaua uucagaggcg uacguucacg ugaaucagua cgauaucguc   2220

uuggacguac ugaucgugaa ccagaccaac gacacguugc aaaauuguac uuuagagcug   2280

gcaacguugg gcgacuugaa guuggucgaa aaaccucaac ccgugguucu ggcgccuaaa   2340

gauuucugua acaucaaagc aaacguuaag guugcuucca cugaaaacgg uauuauuuuc   2400

ggcaacauug ucuaugacgu caccggugcc gcgucugaca gaaauguggu gguuuugaau   2460

gauauacaca ucgauauaau ggacuacaua guaccagcga guuguaccga cacagaguuu   2520

augcgcaugu gggcggaguu ugaguggagg aacaagguaa cugucaacac gucguugaca   2580

gaucugaacg aauacuuaaa acaccugauc aagaguacca acaugaagug ucugacgccg   2640

gaaaaagcgc ugucaggcca gugcgguuuc auggcugcca acauguacgc caaaucuauu   2700

uuuggugaag acgcuuuggc caauuugagu auagaaaaac ccuucaacaa accagaagcu   2760

ccuguacagg gucauaucag gauaagggcc aaaagucagg guauggcuuu gaguuuagga   2820

gauaaaauaa acaguaguca gaaggcugga cuucaaacaa aaguugcggc ggcauaa      2877
```

<210> SEQ ID NO 31
<211> LENGTH: 1716
<212> TYPE: RNA
<213> ORGANISM: Sitophilus granaries

<400> SEQUENCE: 31

```
cauucuuguu guauaaaauu uccugauguc gcugcagcgg uuauaccaau uuugguagag     60

uuuuuaucag auaauaauga gcuagccgcu gcugaugugu uaguuuuugu aagagaagcc    120

auacaaaaau uugaggcacu uagaccaauu auuauugaga aacuucuuga agcguucaag    180

gauauaaaau cgguaaaagu acauagagcu gcacugugga uucuuggaga auaugcuacg    240

ucaguugcug auauagaguc ggucauaaaa gaggugacgu auacauuggg ugaaggaucc    300

cuugucgugg cugaacacag gcucaaccaa ggcgaggugg acgaaaaaca aauagaaaau    360
```

```
aucgggaacg guccagucgu gacuacucua gugacgucag acgguacuua cgcuacucaa    420

ucggccuuua acaccguuca gaaaucgaaa aaagaaaggc cgcccuuaag gcaguaccuu    480

auggauggag auuucuuuau uggagccgcu cuggcuucga cuuugaccaa acuggcuuug    540

agauuugguc agcuaguguc accggaaaga acaaacagau uugacgcgga agucauguug    600

auuauggcgg gaauacugca uuuaggccaa ucaggcuugc caaccaaauc gaucacgaac    660

gacgacaggg accacaucuu gcucuguuug aagguggugu cugacagauc gcccgucauu    720

guucagaucu ucaccgacua cugucgaaag gccuuaaacg acaugcuauu ggccaaagag    780

cgcgaggaag cguccaauca gaaggccaaa gaaaaaacag ggcacaaaau ucaaacggac    840

gauccgauca auuucauuca gcuggagacu gauaagggug gagaauuggg cgagaacgua    900

uucgaaacgu cguuaucgca agcgcugauu gggggaagag ccgcgggcgg ggacacuggu    960

uuagguccaa auaaacugga caaagucacu caacucacag guuucucgga uccgguauau   1020

ucagaggcgu acgugcacgu gaaucaguac gacaucguuu uggacguacu gaucgugaau   1080

cagaccaacg acacguugca gaacuguacg uuagagcugg caacguuggg cgaccugaaa   1140

uugguggaaa aaccucaacc cguuguuuug gccccuaaag auuucugcaa uauuaaagca   1200

aacguuaagg uugcuuccac ugaaaauggu auuauauucg gcaacauugu cuaugacguc   1260

accggcgccg cgucugacag aaaugucguc guuuugaacg acauacacau agacauuaug   1320

gacuacauug ugccagccag uugcaccgac acagaguuua ugcgcaugug ggcggaauuu   1380

gagugggaga acaagguaac ugucaacaca uccuugacag aucuaaacga auaccuaaaa   1440

caccugauca agaguaccaa caugaagugu cugaccccag aaaaagcccu gucgggccag   1500

ugcggcuuca uggcugccaa cauguacgcu aagucuauuu uuggugaaga ugcguuagcc   1560

aauuugagua uagagaaacc cuuuaacaaa ccagaagcuc cuguacaggg ucauaucagg   1620

auaagggcca aaagucaggg uauggcuuug aguuuaggag auaaaaauaaa uaauagccaa   1680

aaggcuggac uucaaacuaa aguugccgca gcauaa                             1716
```

<210> SEQ ID NO 32
<211> LENGTH: 2880
<212> TYPE: RNA
<213> ORGANISM: Ceuthorrhynchus assimilisnarius

<400> SEQUENCE: 32

```
augacgaacg uagaacagcc cuguuacacc cuaaucaacg ugucuuccga uacagagccc     60

uacaaugaaa ugcaucuaaa aagugauuua gaaaaaggug acacagacca aaaaauagaa    120

gcccucaaaa agacuauucg caugauacua gcaggagaac gccuaccgcc agguuuccug    180

augauaauua uucguuacgu acuuccuuua caagaccaua ccgccaaaaa auuauuacua    240

auuuuuuggg aaauuguucc uaaaacaaca ccagauggua aacuuuuaca agaaaugauu    300

cugguuugcg augcuuacag aaaagauuug caacauccaa acgaauuuuu gagaggguca    360

acacugaggu uuuuguguaa acuuaaggaa ccugaauuac uggaaccacu uaugccauca    420

aucagagcuu guuuggagca cagacacagc uaugucagaa gaaaugcugu uuuagcaaua    480

uuuacuauuu aucgcaauuu ugaauuucua auuccugacg cuccagaacu uauuucaaau    540

uacuuagaua gcgaacaaga uaugucgugc aaaaggaacg ccuuuuuaau guugcuacau    600

gcugaucaag acagagcuuu aucuuauuug agcucuugcu uagaucaagu uacuucuuuu    660

ggagauauuu uacaacuggu uauuguagaa cugauuuaua agguuuguca uaccaaccca    720

ucagaaagau ccagauucau ccguugcaua uacaauuugc uaaacucuag uagugccgca    780
```

```
guaagauaug aagcugcagg cacucuuauu acauuaucca gugccccuac ugcuaucaga    840

gcggcggcuu cuuguuacau ugauuuaauu gucaaggaga gcgacaauaa uguuaaacua    900

auuguuuugg auaaguuggu ugcccuuggc gaacauccaa ccuauaacag gguuuugcag    960

gaucucguua uggauauacu aagaguuuug aguaguccug auuuagaagu gagaaggaaa   1020

acuuuaaauu uagccaugga acuagugaau ucuagaaaua uugaggaaac uguuuuguuu   1080

uugaaaaaag aaguuucaaa aacuuuagau ucugaacaug aagauacagg caaauauagg   1140

caacuucuug uaagaacuuu gcauuccugc uguauuaaau uuccugaugu ugcugccaca   1200

gugauuccag uuuuggugga auuuuugucu gauaccaaug aguuagcugc ugcugauguu   1260

uugguguuua ucagagaagc uauacagaaa uuugaaaauu ugcgagcacu uauuauugag   1320

aaacuucuug auucauuuaa ggauauuaaa ucugucaaag uacauagagc cgccuugugg   1380

auuuugggug aauaugccac aucuguuccu gauauugaag caguuauaaa agagauaaca   1440

cuuacucuag gagaaggcuc acuaguugca gcagaaaauc gccuuaacca aggagauguu   1500

gcggaaaaua aaccagaagg agcaagcagu aguggcccug uuguuacuac ucuaguaacu   1560

ucagauggca cauacgcuac ucaaucugca uucaauucug uccaaaaguc cacaaaagaa   1620

aaacguccac cucuucgcca auauaugauc gaugggggauu ucuuuauugg ggcuucuuua   1680

gcuucaacaa uaacuaaaau agcuuuaaga uauggcaacc uugugacacc ugaaaaacgu   1740

aaccgauuug augcugaaau uaugcuuauu augagcggcg uuauucauuu gggacaauca   1800

ggucuaccaa caaaaccaau caccaacgac gaccgcgauc auauuuuauu uugucucaga   1860

guuuuaucug acaggucacc aaucauaauu gaaauauuua cugaauauug cagaaaggcu   1920

cuuaacgaua ugcuauuggc caaggaauua gaggaagcua gcaaccagaa agcuaaagaa   1980

aaaaaaggca cuaaaaucca uacagacgau ccaaucaauu ucuugcaacu ugaaacagac   2040

aaagguggag aauugggaga aaaugucuuu gaaaccucuc ugucacaggc auugguuggu   2100

ggacgaacug gcggcgggga ugguuuaagu accaauaaau uaaacaaagu uacgcaacuc   2160

acagguuucu cagauccugu uuaugcugaa gccuauguuc acguuaacca auacgauauu   2220

guauuggaug uuuuaauugu aaaucaaacu aaugacacuu ugcaaaauug cacguuagaa   2280

uuggcaacgc ugggugauuu aaaacuggua gagaaaccac aaccuguagu guuggcaccu   2340

aaagauuuuu gcaauauuaa agcaaauguu aagguugcau cuacagaaaa ugguauaauu   2400

uuugguaaca uuguauacga caucacugga gccgccucag auagaaaugu uguagucuua   2460

aaugacauac auauugacau uauggacuau auagugccag ccaacuguaa cgauacugaa   2520

uuuaugcgaa ugugggcuga auuugaaugg gaaaacaagg uuaccgugaa uacucagcua   2580

acagaccuaa acgaauaccu aaaacaccua auuaaaagca caaacaugaa auguuugacu   2640

ccggaaaaag cauuaucugg ucagugugga uucauggcug ccaauaugua ugcaaaaucu   2700

auuuuuggag aagaugcuuu ggcuaauuug aguauugaga agccguuuaa caagccagau   2760

gcuccuguuc agggacauau uaggauaaga gccaaaaguc aagguauggc guuaagcuug   2820

ggagacaaaa ucaacagcag ccaaaaggcu caacaacaaa acaaaguugu ugcugcauaa   2880
```

<210> SEQ ID NO 33
<211> LENGTH: 1005
<212> TYPE: RNA
<213> ORGANISM: Rhyzoperta dominica

<400> SEQUENCE: 33

```
cuaucuauug ugaaaguauu ugugcaagaa ugucgaaaug cccugaacga aaugcuucuu     60

gcugaagaag aggaggagca aacaacaaag aaggcuaaag aaaaagccgg gaagaaaauu    120

caagcugaug auccaauuag uuuuaugcag cugcaaucug auaagucagg ugaauuaggu    180

gacaacaucu uugaaaccuc acucucacaa gcacuugcug guggccgucc ugguacagcu    240

gaccuagcag cuuccaucag caaauuaaac aaaguaacac aauuaacugg cuucucagau    300

ccaguguaug cugaagcuua uguacaugua aaucaguaug auauugugcu ggauguuuug    360

auugugaauc agacuaauga uacuuuacaa aacugcaccu uggaacuggc gacauuaggu    420

gaucuaaaac uuguugagaa accgcagccu guugugcuug caccuaaaga uuucuguaau    480

auaaaggcaa auguuaaggu ugcaucuaca gaaaauggua ucauuuuugg aaacauugug    540

uaugauauua cuggugcugc cucagauaga aauguuguug uuuugaauga cauacacauu    600

gacauuaugg auuacauugu uccugcaucu uguaaugaua cugaauuuag acagaugugg    660

gcagaguuug aaugggaaaa uaagguuucu gugagcacca cauugacaga uuuagcagaa    720

uaucucaaac ucuugauuaa gaguacaaau augaagugcu uaaccccaga gaaggcccuu    780

ucuggacagu guggauuuau ggcagccaau auguaugcca agucuauauu uggugaagau    840

gccuuggcua auuugaguau ugagaagcca uuuaauaaac ccgaugcucc ugucaguggu    900

cauauaagaa uaagggcuaa aagucagggc auggcucuca gccugggaga uaagaucaau    960

augacucaaa aggacagcca aacaaaggug guugcugcug cuuaa                   1005
```

<210> SEQ ID NO 34
<211> LENGTH: 2871
<212> TYPE: RNA
<213> ORGANISM: Phyllotreta nemorum

<400> SEQUENCE: 34

```
augacggcgg ucgagcagcc cuguuacacu uuaauuaauc uuccgaccga uucggagccu     60

uacaaugaaa ugcaauugaa aauggaccuc gaaaagggcg aagucaaagu aaagauaagg    120

gcuuuggaaa gaaucauaca caugauauug gcaggcgaga gauugcccaa cggauuccug    180

augacaauca uacgaaacgu uuugccccua caagaucacc uggccaagaa acuuuugcuc    240

auuuuuuggg aaaucgugcc gaaaaccacc cccgacggua aauuacugca ggaaaugauc    300

cuagucugug acgccuacag aaaggaccug cagcacccca acgaauuuuu gaggggcucc    360

acauugagau uccuaugcaa gcugaaggag cccgagcugu uggagccucu gaugcccagc    420

auucgaauuu gccucgaaca caggcacagc uacguucgaa ggaaugccgu ucuggccauu    480

uuuacgauau acaagaauuu cgaauuccuc auuccagacg ccccugaauu gauuucuacu    540

uaucuagacg gcgagcaaga uaugucuugu aaaagaaacg cuuuccuuau gcuuuugcau    600

gccgaccaag aucgagcccu cacuuaccua uccaauugcu uagaucaagu ggcuucuuuu    660

ggggauauuc uacaguuggu uauuguugaa uugauauaca aagugugcca cuccaacccc    720

gccgagagau ccagauucau ucgaugcaua uacaaucuau uaaauucgag caguccugcu    780

guucgguacg aggccgccgg uacucugauu acucugucca gcgcuccgac agccaucaaa    840

gccgccgcua guuguuacau cgaauugauc auuaaagaga gcgacaacaa cgucaaauug    900

aucguuuugg auagauugau cgccuuaaag gagcauccca gccacgagag aguccugcag    960

gauuugguua uggauauauu gagaguuuua ucggcuccug auuuggaagu gcgaaagaaa   1020

acacuuaauu uagcgcugga auuggugucc ucucguaacg ucgaagaaau ggguguuugug  1080

cugaagaaag aggugucuaa aacuguggac agcgaacaag aagacaccgg gaaauauagg   1140
```

```
caauuguugg ucagaacauu gcacuccugc ugcaucaaau uccccgauau agcugcaacg   1200
gucauuccug uuuugaugga auuccugucc gauagcaacg aauuagcggc cacugaugug   1260
uugcuauuuu ugagggaagc cauacagaaa uucgauaaau uagagccgcu cauuaucgaa   1320
aaauuauugg agacauucaa agacaucaaa ucugugaaag uacaucgagc ugcucuuugg   1380
auacugggcg aauacgccac gucgacuggc gacauugaag ccgucaucaa ggagaucguu   1440
caaaccuugg gcgaaugccc auuguuggag acugagcaga agaguauauc ugguaacacg   1500
gaugaaagug cgccgguuca ugcaccagcu ggggcuacca cuuugguuac uucagaugga   1560
acguacgcca cucagucugc uuucaacgug gccagcaaau cgacgaaaga gaagagaccu   1620
ccauugaggc aauaccugau ggacggagau uucuucauug ccgcuucucu ggcuucuacu   1680
uuaaccaaac uggcuuugag guauggcgaa aacguuuccg cuuccgauag gaauaaauuc   1740
gacgccgaag uuaugcucau uauggcuggc auuuugcauc uaggcaaauc agguuugccc   1800
guaaaaccga uaaccaacga cgacaacgac cacauccucu ucugccugcg cgugcuaucc   1860
gaucgaacgg accccgucau ccaaguauuc ucgagccucu gccgcaacgc ccucaacgac   1920
augcugcuag ccaaggaaac cgaagaggcg accgaucaaa aaucccgcga aaaaucccga   1980
gccgccgucc aaaccgacga cgccaucacc uucgugcagc uggaguccga ucgaagcggc   2040
gagcucggcg aaaacauguu ugaaaccucc cucucgcagg cccucauggg cggcaagacg   2100
gcccaauccg acucgaccau cggcucgagc aaacugaaca agaucgccca gcugacgggc   2160
uucucggauc ccgucuacuc cgaagcguau gugcacguca aucaguacga uaucgugcuc   2220
gacgugcugg uggugaacca aacgagcgac acgcugcaga acugcacgcu cgaauuggcg   2280
acuuugggcg auuugaagcu gguggagaag ccgcaacccg ucgugcuggc gccgaaggac   2340
uuuugcaaca ucaaggcuaa cgugaaggug gcuucgaccg agaacgguau cauauucggu   2400
aacauugugu augacgugac gggcgccgcg ucggacagga acgucgucgu uuugaacgac   2460
auucauaucg acauuaugga uuacauuguu ccggcgucgu gcaccgauuc ggaguuuaug   2520
aggaugaggg cugaauucga augggagaau aaggugaccg ucaauacgcc gcuuacagau   2580
cucaacgagu accuggagca uuugcuaaag aguacuaaca ugaagugucu gacgucugag   2640
aaggcgcucg gagggcaaug cggcuucaug gccgccaaua uguacgcaaa aucgaucuuu   2700
ggggaagacg cccuggcgaa uuugagcauc gagaagccgu ucaacaagcc ggacgcgccc   2760
gucgccgggc acauuagaau ucgugccaaa agucagggua uggcuuugag uuugggcgac   2820
aaaaucaaca ugacgcagaa agggacgcaa aguaaggucg uugccgcgua a            2871
```

```
<210> SEQ ID NO 35
<211> LENGTH: 2868
<212> TYPE: RNA
<213> ORGANISM: Psylliodes chrysocephala

<400> SEQUENCE: 35

augacugccg uugaacaguc uuguuauacu uuaauuaauc uaccaacuga uucggagccc     60
uacaaugaaa ugcagcucaa aauggaccuc gaaaagggcg agguuaaggu aaaaaauaaga   120
gcacuugaaa ggauuauaca caugauauua gcuggagaaa gauuaccaaa cggauucuua   180
augacuauua uaaggaaugu ccuuccccuu caggaucauu uagcuaagaa auuacuucua   240
auuuuuuggg aaauuguacc aaaaacuuca ccugauggca aauuauuaca agaaaugauu   300
uuagugugug augccuacag aaaagaucug caacacccaa acgaauuucu ucgagguucu   360
```

```
acuuuaagau ucuuauguaa auuaaaagaa ccagaacugc uagaaccucu aauggcuagu    420
aucagagccu guuuggauca caggcacagu uaugugcgaa gaaaugcagu uuuggcuauu    480
uuuacaauuu auagaaauuu ugaguucuua auuccugaug cacccgaacu uauuucuacu    540
uauuuagaug gugagcagga uaugucuugc aagagaaaug cuuuucugau gcuuuuacau    600
gcugaucaag auagagcacu gucuuauuug gcaaauuguc uagaucaagu uacaucauuu    660
ggagacauuc ugcaauuggu cauuguugaa uuaaucuaua aaguuugcca uucaaauccc    720
acagagaggu caagauuuau ccgcugcauu uacaaucuau uaaauucaag caguccugcu    780
gucagauaug aagcugcugg uacacuugua acacuuucaa gugcucccac agcaguaaaa    840
gcagcugcua guuguuauau ugaacuaauu aucaaggaaa gugauaauaa uguaaaguug    900
auugucuugg acagauugau ugcccuuaag gaacauccca gccaugaaag gguuuugcaa    960
gauuugguua uggauauauu aagaguguug caagcuccug acuuggaagu ucgcaaaaag   1020
acuuuaaacc uagcacuuga acugguauca ucucguaaua uagaagaaau gguuuugguu   1080
cuuaaaaagg agguaucaaa aaccguagau agcgagcacg aagauacagg aaaauacagg   1140
caguuacuug uuagaacacu ucauucuugu uguauaaaau ucccagaugu agcuguaacu   1200
gucauuccug uuuuaaugga auuuuugucu gauaguaacg aguuagcugc uacugacgug   1260
uuacuauuuu ugagagaggc cauacagaag uuugauaauc ugcaaccacu uauuauugag   1320
aaacuucuag aaacauucaa agauauaaaa ucuguuaaag ugcauagagc agcucuuugg   1380
auauugggag aauaugccac uucugucuca gacauugaag cuguuauuaa agaaauuaau   1440
caaaccuuag gagaagcucc ucuguuggaa acugaacaaa aacuaauuuc uggagagaca   1500
gacgacacaa cuacaguucc aacaggugga gcuacaacuu ugguuacuuc agaugguacu   1560
uacgccacuc agucugccuu uaauucaguc aguaaaucuu caaaagaaaa acgaccuccu   1620
cugaggcaau aucuuaugga uggugauuuu uuuauaggag cguccuugac uucuacucua   1680
accaaauuag cuuuaagaua uggucaaauu gccucagcug cugauagaaa uagguuugau   1740
gcugaaguca ugcuuauuau ggcagguauc auacauuuag gcaaaucagg uuuaccgaca   1800
aaaccaauaa ccaacgauga caaagaccac auacuuuuuu gcuugcgugu caucucagac   1860
cgcaccgacc caauaauaca aauuuucucu acucuguguc gaucugcucu caaugacaug   1920
uugauagcga aggaagcgga agaagccacg acucaaaaau cuaaagaaca auccagacac   1980
acuauccaaa cagaugacgc uaucaguuuc cuucaauuag aagcggacaa gagcggcgaa   2040
cuuggggaaa auguauucga aaugucuuua ucacaagccu uggucggagg uagagguggc   2100
caaacagacu cccuaaucag uuccaauaaa uugaacaaga uaacacaguu gacuggauuu   2160
ucggaucccg uauauucaga agcuuacguc cacguuaauc aauacgauau aguucuugau   2220
guuuuaauag ugaaucaaac gaacgacacu cuucaaaauu gcacgcugga acuggcgacg   2280
cugggcgauu ugaaacucgu agaaaaaccu caaccugucg uacucgcgcc uaaagauuuu   2340
uguaauauua aggcgaacgu uaagguagcu uccacagaaa acggcauuau auuugguaau   2400
auuguuuacg acgucaccgg ugccgcuuca gauagaaaug uaguguuuu aaaugacauu   2460
cauaucgaua uuauggauua uauuguuccc gcgagcugua cagauaccga guuuaugagg   2520
augugggcag aauuugaaug ggaaaauaag gucacuguaa auacaccucu cacagaccuc   2580
gccgauuacc uugaccaucu cuugaaaagu acaaacauga aaugucugac uuccgaaaaa   2640
gcccuuagcg gucaaugcgg auuuauggcc gccaauaugu augccaaauc uauuuucgga   2700
gaagacgcgc uugcaaauuu gagcauagaa aagccuuuca acaaaccaga ugcaccaguc   2760
```

gcagggcaca ucaggauuag agcuaaaagu caaggaaugg cuuugaguuu aggugauaaa 2820
auaaauauga cacaaaaagg aacucagagu aaaguagcug cugcauga 2868

<210> SEQ ID NO 36
<211> LENGTH: 2871
<212> TYPE: RNA
<213> ORGANISM: Phyllotreta striolata

<400> SEQUENCE: 36
augacggcgg ucgaacagcc cugcuacacu uuaaucaauu ugccgaccga uucggagccu 60
uacaaugaaa ugcaauugaa aauggaucuc gaaaagggcg aaaucaaagu aaagauaagg 120
gcuuuggaaa gaaucauaca caugauacug gcuggcgaga gguuaccaaa uggguuccuc 180
augacaauca uacgaaacgu ucugccccua caagaucacc uugccaagaa gcuguugcuc 240
auuuuuuggg aaaucgugcc gaaaaccacc cccgauggca aauuacugca ggaaaugauc 300
cuggugugcg acgccuacag aaaggaccug cagcacccca acgaauucuu gcgagggucu 360
acauugagau uccugugcaa gcuaaaggag cccgagcugu uggagccucu gaugcccagc 420
auacgaauuu gccuggaaca cagacacagc uacguucgca ggaaugccgu ucuggccauu 480
uuuacgauau acaagaauuu cgaauuucuc auucccgacg ccccugaauu gauuucuacu 540
uaccuagaug gcgaacaaga caugucuugu aaaaggaacg cuuuucuuau gcucuugcac 600
gccgaucaag aucgagcccu cacuuaucua uccaauuguu uagaucaagu cgcuuccuuc 660
ggggauaucc uucaguuggu uaucgucgaa uugauauaca aggugugcca cucuaacccc 720
accgagagau ccagauucau ucgaugcaua uacaaucugu uaaauucgag caguccugcu 780
guuagauacg aagcggcagg uacucucauu acuuugucca gcgcuccgac ugcuauaaaa 840
gccgccgcca guuguuacau cgaauugauc auuaaagaga gcgacaacaa cgucaaauug 900
aucguuuugg auagauugau cgcguugaag gaacauccga gccacgagag aguccuacag 960
gacuugguua uggauauauu gagaguguua ucggcucccg auuuggaggu gcgaaagaaa 1020
acgcuuaauu uagcgcucga auuggugucc ucucguaacg ucgaagaaau ggugguuugug 1080 cugaagaagg aggugucgaa gaccauggau agcgaacacg aagauaccgg gaaauacagg 1140
caacuguugg ucagaacguu gcauucuugu ugcaucaaau uccccgauau agcugcuacg 1200
gucauucccg uucuaaugga guuccugucc gauagcaacg aauuggcggc caccgaugug 1260
uugcuauuuc ugagggaagc cauacagaaa uucgauaauu uggagccgcu cauuaucgag 1320
aaauuauugg agacauucaa agacaucaaa ucggugaaag uucaucgagc cgcucuuugg 1380
auauugggcg aauacgccac gucgacuggc gacaucgaag ccgucaucaa agagaucguu 1440
cacacguuag gcgaaugccc auuguuggag accgagcaaa agauuauauc ugguaguacu 1500
gaggaaagcg cuccgguuca ugcaccugcc ggagcaacca cuuugguuac cucagaugga 1560
accuacgcca cucaaucugc cuucaacgug gccagcaaau cgaccaaaga gaagagaccu 1620
ccguugaggc aguacuuaau ggacggagau uucuucaucg ccgcuucucu ggcuucuacu 1680
uugaccaaau uggcuuugag guacggcgaa aacgcuucac cuuccgauag gaacaaauuc 1740
gacgccgaag uuaugcucau cauggccgga auucugcacc uaggcaaauc agguuugccg 1800
guaaaaccga uaacuaacga cgacaacgac cauauucucu ucugccugcg cgugcugucc 1860
gaucgcacgg agcccguggu gcaaguguuc ucgaggcucu gccgcaacgc gcucaacgac 1920
augcugcugg cgaaggagac cgaagaggcg accgaucaga aaucgcgcga gaaaucccga 1980

```
gcggccgucc agaccgacga cgccaucacc uucgugcaau uggaguccga ucgaagcggc   2040

gagcucggcg agaacguguu cgaaaccucc cugucgcaag cgcugauggg cggcaaaacg   2100

ggccaauccg auucgagcgu aggaucgagu aaacugaaua aaaucgccca gcugacgggu   2160

uucucggauc ccguuuacuc cgaagcguac gugcacguua aucaguacga uaucgugcuc   2220

gaugugcugg uggugaacca gacgagcgau acgcugcaga auugcacguu ggaauuggcg   2280

acgcugggcg auuugaaguu gguggagaag ccgcagcccg ucguacuggc gccgaaggac   2340

uucugcaaua uuaaagcuaa cgugaaggug gcuucgaccg agaaugguau uauauucggu   2400

aacaucgugu acgauguaac cggagccgcu uccgacagga acguugucgu uuugaacgac   2460

auacacaucg auauaaugga uuacauuguu ccggcaucuu gcaccgauuc ggaguuuaug   2520

aggauguggg cugaauucga gugggagaau aaggugaccg ucaauacgcc guugacggau   2580

cucaacgagu accuggagca ucugcugaag aguacuaaca ugaagugccu gacgucggag   2640

aaggcgcugg gcgggcaaug cgguuucaug gcggcuaaua uguacgcgaa aucgaucuuu   2700

ggagaggacg cccuggcgaa uuugagcauc gaaaagccgu uuaauaagcc ggacgcgccc   2760

gucgccgguc acauuagaau ucgggccaaa agucagggua uggcuuugag uuugggcgac   2820

aagaucaaca ugacgcagaa agggacgcaa agcaaggugg ucgccgcgua a            2871
```

<210> SEQ ID NO 37
<211> LENGTH: 2868
<212> TYPE: RNA
<213> ORGANISM: Leptinotarsa decemlineata

<400> SEQUENCE: 37

```
augacuacca uggaacagcc uuguuacaca cucaucaauu uuccgacaga uucugaacca     60

uauaaugaaa ugcaacucaa aacggauuua gagaagggcg augugaaagu caaaauacga    120

gccuuagaaa gaaccauuca caugauuuug gcaggagaac gccugccgaa cgguuucuua    180

augacgauua ucagguaugu ucugccgauu caggaucauu uggccaaaaa gcuguuguua    240

auuuuuuggg aaauugugcc aaagaccuca ccugacggaa aacugcuaca ggaaaugauu    300

cucguuugug augcauaucg gaaagacuua caacauccca augaauuccu caggggguca    360

acgcugaggu uucuuugcaa acuuaaggag ccugaguugu uggagccucu gaugccaagc    420

auccggaaau guuuggagca caaacacagu uaugugagga gaaaugcugu uuuagccaua    480

uucaccauuu aucgcaauuu ugaauuucuu auaccugaug cuccugagcu gauuuccaac    540

uaucucgaug gagaacaaga caugucaugc aaacgcaaug cuuuucucau gcuucuacau    600

gcagaucagg agagggcuuu gucguauuua gcgucuugcc uggaccaagu uacuucguuc    660

ggugacaucu uacaguuggu aauuguggag uuaauauaca aagucuguca cacaaauccc    720

ucagaacguu cccgauucau cagaugcauu uauaacuugc ugaauuccag uaguccugcg    780

guucguuacg aagccgcagg gacucuggua acucuaucca gugccccaac ggccaucaaa    840

gcugccgcca gcuguuacau cgaacucauc aucaaagaaa gugauaacaa cgugaaacuc    900

auuguucugg acagacugau ugcguugaaa gaucacccca gucacgagcg agucuugcaa    960

gaccucguua uggacauauu aaggguucuc ucggccccgg auuuggaggu acgcaagaag   1020

acucuuaguu uagccaugga guugauuucg ucacguaaua uugaagagau gguacugauu   1080

uuaaagaaag aggucucuaa aacgcuugac agugaacacg aagacacagg aaaguaccgu   1140

caguuauuag uucgcacguu gcauuccugc uguaucaaau uuccagaugu ggccguuacc   1200

guaauuccag uguugaugga guuuuugucc gacaguaaug aauuggcagc cacugacgua   1260
```

```
cuuguguuug ugagagaggc cguacagaag uuugagaauu ugcagccucu aguuauagag   1320

aaauuauugg aaacuuucaa ggauaucaaa ucuguaaagg uucaccgugc agcccuuugg   1380

auauugggag aauaugcuac cucuguuagu gauauagaga ugguaaucaa gcaaauuaau   1440

caaacuuugg gugauugccc ccucuuggaa gcggagcaga gacucguuuc uggagaugca   1500

gaggaaaaua uuucaaacau aaguaguacc acuacaacgu ugguuacauc ugaugggacu   1560

uacgcuaccc agucaucuuu caauacaguu cacaaaucaa guaaagaaaa gaggccucca   1620

cuucgucaau auuuaaugga cggcgauuuc uuuauuggag ccucgcucgc uuccacauug   1680

acaaaauuag cuuugcgcua cggaaaucuc acuucucccu cacaaaggaa uagauuugac   1740

acugaaguca uguugaucau ggcaggaauu guucauuugg gaaaaucagg cuugccaacg   1800

aaaccgauca cgaaugacga uaaggaucac auccuguucu gucugagggu ucucuccgau   1860

cguacuuccg ccaucauuca gauauucaca gagcgcugcc ggcucgcucu caaugacaug   1920

cuugucgcca aagaagcaga agaggcgucg acucugaaga cgaaagagaa auccggcaau   1980

acgauccaaa cagaugaccc gauuagcuuc cuccagcuag aggccgacaa gaauggagaa   2040

cuuggcgaaa acguauuuga gaccucgcug ucgcaagccc ucgucggugg aagaggcagc   2100

gcggcagauu cugccacagg aacaaauaag uugaacaaga uaacgcaguu gacagguuuu   2160

ucggaucccg uuuauucaga agcuuauguc cacgucaacc aguacgauau ugugcuggac   2220

guuuugaucg ucaaucaaac uaaugauacu cugcaaaauu guacuuugga gcuggcgacg   2280

uugggagauc ugaaacuugu cgaaaaaccu cagccaguag uucuugcucc caaagacuuc   2340

uguaacauca aagcccacgu aaagguugcu uccacugaaa acggaaucau cuuuggaaac   2400

aucguuuaug acgugacggg cgcggccuca gacaggaacg uagucguccu caaugacauc   2460

cacaucgaca ucauggacua uauuguucca gcgucuugua ccgauucaga auuuaugagg   2520

augugggcug aauucgaaug ggaaaauaag gugacuguca acacaccucu gacggaccuu   2580

gccgacuacu uggagcaccu cauuaagagc accaacauga aaugcuugac gccagaaaag   2640

gcgcucagcg gucagugugg uuucauggca gccaauaugu acgcuaaauc cauauuugga   2700

gaagacgcuu uggccaauuu gaguauagag aaaccguuua acaaaccaga agcaccugua   2760

gcuggacaca ucagaaucag ggcuaagagu cagggcaugg ccuugagcuu aggagacaaa   2820

auaaauauga cucaaaaagg cauaccaagu aagauuguug caucuuga               2868
```

<210> SEQ ID NO 38
<211> LENGTH: 20
<212> TYPE: DNA
<213> ORGANISM: Meligethes aeneus

<400> SEQUENCE: 38

```
gtaacacaat tgaccggttt                                                  20
```

<210> SEQ ID NO 39
<211> LENGTH: 20
<212> TYPE: DNA
<213> ORGANISM: Meligethes aeneus

<400> SEQUENCE: 39

```
tactttgctg ttgtgcagac                                                  20
```

<210> SEQ ID NO 40
<211> LENGTH: 20
<212> TYPE: DNA

<213> ORGANISM: Sitophilus oryzae

<400> SEQUENCE: 40
accttgcatt cttgctgtat 20

<210> SEQ ID NO 41
<211> LENGTH: 20
<212> TYPE: DNA
<213> ORGANISM: Sitophilus oryzae

<400> SEQUENCE: 41
agggccttcc tacaatagtc 20

<210> SEQ ID NO 42
<211> LENGTH: 20
<212> TYPE: DNA
<213> ORGANISM: Sitophilus granaries

<400> SEQUENCE: 42
gaaaggcctt aaacgacatg 20

<210> SEQ ID NO 43
<211> LENGTH: 20
<212> TYPE: DNA
<213> ORGANISM: Sitophilus granaries

<400> SEQUENCE: 43
ggatgtgttg acagttacct 20

<210> SEQ ID NO 44
<211> LENGTH: 23
<212> TYPE: DNA
<213> ORGANISM: Ceuthorrhynchus assimilis

<400> SEQUENCE: 44
cctgacgctc cagaacttat ttc 23

<210> SEQ ID NO 45
<211> LENGTH: 21
<212> TYPE: DNA
<213> ORGANISM: Ceuthorrhynchus assimilis

<400> SEQUENCE: 45
aacaccaaaa catcagcagc a 21

<210> SEQ ID NO 46
<211> LENGTH: 20
<212> TYPE: DNA
<213> ORGANISM: Rhyzopertha dominica

<400> SEQUENCE: 46
tgaaacctca ctctcacaag 20

<210> SEQ ID NO 47
<211> LENGTH: 20
<212> TYPE: DNA
<213> ORGANISM: Rhyzopertha dominica

<400> SEQUENCE: 47
aattagccaa ggcatcttca 20

<210> SEQ ID NO 48
<211> LENGTH: 20

<212> TYPE: DNA
<213> ORGANISM: Phyllotreta nemorum

<400> SEQUENCE: 48
ggagccttac aatgaaatgc 20

<210> SEQ ID NO 49
<211> LENGTH: 20
<212> TYPE: DNA
<213> ORGANISM: Phyllotreta nemorum

<400> SEQUENCE: 49
gctggacaga gtaatcagag 20

<210> SEQ ID NO 50
<211> LENGTH: 20
<212> TYPE: DNA
<213> ORGANISM: Psylliodes chrysocephalus

<400> SEQUENCE: 50
tgtcagatat gaagctgctg 20

<210> SEQ ID NO 51
<211> LENGTH: 20
<212> TYPE: DNA
<213> ORGANISM: Psylliodes chrysocephalus

<400> SEQUENCE: 51
ggcgtaagta ccatctgaag 20

<210> SEQ ID NO 52
<211> LENGTH: 20
<212> TYPE: DNA
<213> ORGANISM: Phyllotreta striolata

<400> SEQUENCE: 52
acttacctag atggcgaaca 20

<210> SEQ ID NO 53
<211> LENGTH: 20
<212> TYPE: DNA
<213> ORGANISM: Phyllotreta striolata

<400> SEQUENCE: 53
tatggcttcc ctcagaaata 20

<210> SEQ ID NO 54
<211> LENGTH: 20
<212> TYPE: DNA
<213> ORGANISM: Leptinotarsa decemlineata

<400> SEQUENCE: 54
gttgatcatg gcaggaattg 20

<210> SEQ ID NO 55
<211> LENGTH: 20
<212> TYPE: DNA
<213> ORGANISM: Leptinotarsa decemlineata

<400> SEQUENCE: 55
cgctggaaca atatagtcca 20